(12) United States Patent
Stanley

(10) Patent No.: US 10,391,297 B2
(45) Date of Patent: Aug. 27, 2019

(54) APPARATUS FOR TREATING A PATIENT HAVING A HEART

(71) Applicant: Cardiola Ltd., Winterthur (CH)

(72) Inventor: Glenn Stanley, Winkel (CH)

(73) Assignee: Cardiola Ltd., Winterthur (CH)

( * ) Notice: Subject to any disclaimer, the term of this patent is extended or adjusted under 35 U.S.C. 154(b) by 19 days.

(21) Appl. No.: 15/303,122

(22) PCT Filed: Mar. 31, 2015

(86) PCT No.: PCT/EP2015/057114
§ 371 (c)(1),
(2) Date: Oct. 10, 2016

(87) PCT Pub. No.: WO2015/155077
PCT Pub. Date: Oct. 15, 2015

(65) Prior Publication Data
US 2017/0028189 A1    Feb. 2, 2017

(30) Foreign Application Priority Data
Apr. 10, 2014  (GB) .................... 1406483.6

(51) Int. Cl.
*A61N 1/36*    (2006.01)
*A61N 1/04*    (2006.01)
(Continued)

(52) U.S. Cl.
CPC ......... *A61N 1/0452* (2013.01); *A61N 1/0484* (2013.01); *A61N 1/36003* (2013.01);
(Continued)

(58) Field of Classification Search
CPC .. A61N 1/36; A61N 1/36003; A61N 1/36014; A61N 1/36031; A61N 1/3625; A61N 1/3627
See application file for complete search history.

(56) References Cited

U.S. PATENT DOCUMENTS

| 6,148,233 A | 11/2000 | Owen et al. |
| 6,450,942 B1 | 9/2002 | Lapanashvili et al. |

(Continued)

FOREIGN PATENT DOCUMENTS

| DE | 602004009262 T2 | 7/2008 |
| EP | 1078649 A1 | 2/2001 |

(Continued)

OTHER PUBLICATIONS

Seo, Akihiko, et al. "A Portable Apparatus for Monitoring Leg Swelling by Bioelectrical Impedance Measurement." Journal of Occupational Health, vol. 39, No. 2, 1997, pp. 150-151., doi:10.1539/joh.39.150.*

(Continued)

*Primary Examiner* — Allen Porter
(74) *Attorney, Agent, or Firm* — Mintz Levin Cohn Ferris Glovsky and Popeo, P.C.; Peter F. Corless; Steven M. Jensen

(57) ABSTRACT

The present invention relates to a method and to an apparatus for treating, diagnosing and/or monitoring a patient having a heart, a heart rhythm comprising periodically repeating Q, R, S and T waves of an electrocardiogram and a peripheral vascular system, said electrocardiogram exhibiting a repeating QRSTQ heart rhythm having a Q-T systole duration, a T-Q diastole duration and an R-R path length, said patient having a pulse rate corresponding to said R-R path length, the apparatus comprising a plurality of electrodes attachable externally or internally to the patient for electrically stimulating the patient non-invasively or invasively, in synchronization with the heart rhythm, by trains of pulses applied to the patient, determining, for cycles of the heart rhythm, a time corresponding to the end of an associated T-wave and applying trains of electrical stimulation pulses within a range of −15% to −1% corresponding to said (Continued)

Figure 1A:
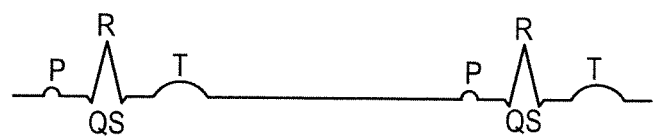

R-R path length before the end of the T-wave and having a train duration selected in the range of 5 to 15% of said R-R path length, so that the train of stimulation pulses ends at at most +5% RR from the end of the T-wave.

18 Claims, 14 Drawing Sheets

(51) Int. Cl.
    *A61N 1/362*     (2006.01)
    *A61N 1/365*     (2006.01)

(52) U.S. Cl.
    CPC ....... *A61N 1/36014* (2013.01); *A61N 1/3625* (2013.01); *A61N 1/36042* (2013.01); *A61N 1/36585* (2013.01); *A61N 1/36592* (2013.01)

(56) References Cited

U.S. PATENT DOCUMENTS

| | | | |
|---|---|---|---|
| 6,832,982 | B1 | 12/2004 | Lapanashvili et al. |
| 7,158,826 | B1 | 1/2007 | Kroll et al. |
| 7,340,302 | B1 | 3/2008 | Falkenberg et al. |
| 7,941,215 | B2 | 5/2011 | Lapanashvili |
| 8,032,207 | B2 | 10/2011 | Lapanashvili et al. |
| 2001/0014816 | A1 | 8/2001 | Hsu et al. |
| 2002/0077688 | A1* | 6/2002 | Kirkland .............. A61N 1/0452 607/142 |
| 2005/0090867 | A1 | 4/2005 | Lapanashvili et al. |
| 2007/0156178 | A1* | 7/2007 | Lapanashvili ....... A61B 5/0456 607/2 |
| 2007/0198064 | A1* | 8/2007 | Lapanashvili ....... A61B 5/0245 607/9 |
| 2007/0225770 | A1 | 9/2007 | Lapanashvili |
| 2007/0233194 | A1 | 10/2007 | Craig |
| 2008/0021504 | A1 | 1/2008 | McCabe et al. |
| 2008/0215114 | A1 | 9/2008 | Stuerzinger et al. |
| 2011/0264160 | A1 | 10/2011 | Lenz et al. |
| 2014/0025136 | A1 | 1/2014 | Stuerzinger et al. |

FOREIGN PATENT DOCUMENTS

| | | | |
|---|---|---|---|
| EP | 1529550 A1 | 5/2005 | |
| EP | 1694404 A1 | 8/2006 | |
| EP | 2526998 A2 | 11/2012 | |
| FR | 2617722 A1 | 1/1989 | |
| WO | WO 01/13990 | * 3/2001 | ............... A61N 1/36 |
| WO | 2006053596 A1 | 5/2006 | |

OTHER PUBLICATIONS

Schwan, Herman P. "Electrical Impedance of the Human Body." NWL Technical Report TR-2199. U.S. Naval Weapons Laboratory. Jan. 1968, doi:10.21236/ad0842306.*

Banedee et al., "Electrical Muscle Stimulation for Heart Failure: where do we Stand?", Journal of Clinical & Experimental Cardiology, 2013, 4:2.

Angelopoulos et. al., "Acute microcirculatory effects of medium frequency versus high frequency neuromuscular electrical stimulation in critically ill patients—a pilot study", Ann Intensive Care, 2013; 3: 39.

Sherry et. al., "Effect of Burst-Mode Transcutaneous Electrical Nerve Stimulation on Peripheral Vascular Resistance", Physical Therapy, 2001; 81:1183-1191.

Nelson et. al., "Noninvasive Measurement of Central Vascular Pressures With Arterial Tonometry: Clinical Revival of the Pulse Pressure Waveform?" Mayo Clin Proc., May 2010;85(5):460-472.

Uk Search Report dated Jul. 17, 2015 in corresponding Application No. GB1406483.6.

International Search Report dated May 12, 2015 in corresponding International Application No. PCT/EP2015/057114.

* cited by examiner

Aortic Pressures

APPARATUS FOR TREATING A PATIENT HAVING A HEART

This application is a National Phase application filed under 35 U.S.C. § 371 of PCT International Application No. PCT/EP2015/05114 with an International Filing Date of Mar. 31, 2015, which claims under 35 U.S.C. § 119(a) the benefit of Great Britain Application No. 1406483.6. filed Apr. 10, 2014, the entire contents of which are incorporated herein by reference.

The present invention relates to an apparatus and a method for treating, diagnosing and/or monitoring a patient having a heart, a heart rhythm comprising periodically repeating Q, R, S and T waves of an electrocardiogram and a peripheral vascular system, said electrocardiogram exhibiting a repeating QRSTQ heart rhythm having a Q-T systole duration, a T-Q diastole duration and an R-R path length, said patient having a pulse rate corresponding to said R-R path length, the apparatus comprising at least first and second electrodes attachable externally or internally to the patient for electrically stimulating the patient non-invasively or invasively, in synchronization with the heart rhythm, by trains of pulses applied to the patient, determining, for cycles of the heart rhythm, a time corresponding to the position of the associated T-wave and applying trains of electrical stimulation pulses generally at the ends of the T-waves for a duration less than the T-Q diastole duration.

A method and an apparatus of this kind is known from the U.S. Pat. No. 6,450,942 and especially from the U.S. Pat. No. 6,832,982 and from the corresponding EP patent 1 078 649 B;

The present applicants have carried out clinical tests with apparatus of this general kind, for example as detailed in the European patent application published as EP 2 526 998 A2 and have conducted extensive studies, clinical trials and research using such apparatus. Experience has shown that patients treated with such apparatus and methods can show truly remarkable recovery from life threatening cardiac conditions, can make more rapid recovery from bypass and other heart surgery, can experience a highly significant improvement in their metabolism and general well-being, can experience significant weight loss and improved body tone and can significantly reduce their dependence on high levels of medication.

Many different aspects of the technology have been investigated and include ways of shaping the preferred biphasic pulses used for the electrical stimulation. The term biphasic basically covers pulses having a positive pulse followed by an associated negative pulse (or vice versa), with the idea being that this change in polarity reduces unwanted bio-physical effects within the patient's body. A way of obtaining biphasic pulses with a preferred shape is set forth in EP 1 529 550 B1.

The technology also includes ways of predicting the position of the T-wave, for example as described in U.S. Pat. No. 8,032,207. This concept is based on the recognition that it is relatively easy to recognize the R-R peaks of a patient's heart rhythm and that it is possible to derive the expected position of the T-wave of the next heart cycle using the so-called Bazett relationship.

Ways have also been considered for enhancing the muscular contraction experienced by the body while reducing the electrical energy required to trigger muscular contraction, see for example U.S. Pat. No. 7,941,215.

Consideration has also been given to varying the electrical stimulation in order to prevent the patient becoming accustomed to it in a way which reduces the desired effect. This is descried in EP 1694404.

In addition it has been realized that the technology is an ideal candidate for "telemedicine. A number of different approaches to this concept, which enables remote control of a patient carried stimulation apparatus and regular patient monitoring from a remote expert center or medical practice, are set forth in EP 05 786 935.6, published as WO 2006/053596. The content of the above referenced patents and applications of the present applicants are incorporated herein by reference.

One of the significant benefits of the apparatus and methods described above is that they work well with externally applied electrodes so that the apparatus and the associated methods are completely non-invasive.

Another aspect of the technology developed to date is that it can be used while the patient is going about his normal daily routine, including at work and stimulation can be carried out essentially without any time limitation. The applicants have many patients who have been undergoing continuous treatment for periods two to three months. It has also been found that after a longer period of treatment, for example of three months, use of the apparatus can be discontinued and the positive benefits endure for a longer period, again of typically about three months, before treatment needs to be recommenced.

Despite all the experience and clinical trials with the apparatus to date there has still been uncertainty regarding how the apparatus actually works in the sense of the mechanism by which treatment with the apparatus affects the human body and leads to the positive benefits.

In the beginning it was believed that the pulsations experienced by the body as a result of muscle contraction had a purely mechanical effect on the pressure of the blood delivered by the heart akin to a resonant phenomenon and led to an augmentation of the blood supply to the coronary arteries. However, it then seemed that the mechanical influence is actually too small to account for the amazing effects that have been achieved. Also there were theories that the applied stimulation has some effect on the autonomic nervous system but the mechanisms were not fully understood. Some practitioners believed the applied electrical stimulation leads to a kind of resynchronization of the human body so that it operates more in line with nature's in-built clock. There have also been theories and attempts to influence the flow of blood through areas of the human body as a result of the application of stimulation to physically separated muscle groups. However, measurements do not support this theory which would expect significant time delays depending on where the body is stimulated in relation to the heart.

More recently the present applicant has arrived at a completely new understanding of the way this form of treatment can affect the human body and have now established that particular benefits can be achieved if the therapy is carried out taking account of the hitherto unrecognized ground rules, which run contrary to accepted understanding. Moreover, having made the relevant recognitions the applicant has now been able to provide evidence which clearly supports their findings, which will be presented later together with the results of clinical studies and clinical evidence regarding the operation of the currently presented apparatus.

Past experiences with the operation of the electrotherapy apparatus described above admittedly showed beneficial results for a proportion of the patients treated; however, by no means for all of the patients treated. It was difficult to predict which patients could be successfully treated.

In view of the foregoing it is thus an object of the present invention to provide an improved and simplified apparatus and method of the initially named kind which provides improved treatment with more general applicability so that a very large proportion of patients treated experience a favorable result and indeed with the treatment itself resulting in less discomfort to the patient, while nevertheless obtaining the desired physical effects and further beneficial effects.

In order to satisfy this and other objects there is provided an apparatus of the initially named kind having the special feature that the apparatus is configured to apply trains of electrical stimulation pulses at a time within a range of −15% to −1% of the R-R path length before the end of the T-wave and having a train duration selected in the range of 5 to 15% of said R-R path length, so that the train of stimulation pulses ends at at most +5% RR after the end of the T-wave.

Recent work by the applicants has led to some remarkable discoveries resulting from the subject matter claimed in the appended claims which run contrary to expectations and which offer the prospect of improved and simplified treatment with more general applicability, so that a substantially increased proportion of patients treated experience a favorable result and indeed with the treatment itself resulting in little or no discomfort to the patient while nevertheless obtaining the desired physical effects.

Moreover, it has been found that the benefits of treatment with the presently proposed apparatus and method can be used to address a wider range of ailments.

The present invention differs from the invention previously claimed, for example in U.S. Pat. No. 6,832,982 in the following respects: a) the start of stimulation is shifted from early diastole to late systole, this is considered a major step contrary to accepted teachings because activating stimulation at any time during systole would be expected to work against the heart and thus lead to an increased heart failure probability, due to increases in workload, blood pressure and heart rate.

However, the exact opposite was discovered. When investigating the matter further, it was discovered that by timing the triggering of muscle stimulation to coincide with the descending phase of the T-wave, such stimulation coincided with muscle sympathetic nerve activity (MNSA which is ECG-synchronized), augmenting (enhancing) its effect on arterial blood pressure and triggering baroreceptor adjustment (via negative feedback to the brain) and down regulation of sympathetic nerve activity which happens to be up regulated in heart failure.

One effect of this is to increase diuresis removing excess water and salt from the patient's body and indeed to such an extent that during initial treatment of patients suffering from acute heart failure the first hours of treatment lead to significant water loss by repeated urination, due to a down regulation of the Renin Angiotensin Aldosterone System (RAAS) triggered by a down regulation of sympathetic nerve activity. The treatment of patients with acute heart failure requires the use of diuretic medication to reduce oedema in the patient's body; however, this medication has the side effect of worsening kidney dysfunction and risking kidney failure. By organizing the electrotherapy in accordance with the present invention diuresis is increased limiting the dose of diuretics needed, thus reducing the load on the heart and speeding up recovery while being kind to the kidneys reducing the risk of kidney failure.

b) The limitation of the duration of stimulation to a range of 5 to 15% R-R, preferably from 8 to 12% and especially at 10% of the R-R path length. The decision to limit the duration of stimulation reflects the recognition:

that decreasing the duration of stimulation from 20% of R-R (contrary to the applicant's own previous belief), unexpectedly led to a decrease in the possibility of unwanted cardiovascular effects, such as increases in heart rate and blood pressure, suggesting that one or both of the following took place in the past:

i) the increased duration of stimulation led to the skeletal muscle contraction being carried over into the next systole (cardiac cycle), due to delayed muscle relaxation.

ii) the longer duration of stimulation prolonged stimulated skeletal muscle blood vessel emptying, thereby reducing blood vessel filling, with a net reduction in blood volume pumped and a build-up in the muscles of systemic vascular resistance increasing metabolytes (via ergo-receptor stimulation).

c) The limitation to the effect that the train of stimulation pulses ends at, at most, +5% R-R after the end of the T-wave, ensures that the stimulation is started in late systole and completed latest within early diastole, so as not to impact on the next systole and to enhance the filling of the stimulated skeletal muscle blood vessels with blood. This leads to an increase in the blood volume pumped largely prevents the buildup of metabolytes in blood vessels and so avoids ergoreflex driven increases in systemic vascular resistance.

The apparatus in accordance with the invention as claimed in claim 1 can be understood in two ways. First of all it is beneficial if the apparatus is designed so that the timing of the start of electrical stimulation can be selected at any time within a range of −15% to −1% of the R-R path length before the end of the T-wave, that the train duration can be selected to be in the range of 5 to 15% of said R-R path length, and that the train of stimulation pulses can be terminated at at most +5% RR after the end of the T-wave. Such an apparatus can operate at any combination of parameters that satisfies these boundary conditions and the precise parameters selected enable an ideal matching of the apparatus to the needs of any particular patient, i.e. personalized care. The quality of that matching can be simply and effectively facilitated by the use of surrogate markers as will be explained further below.

Alternatively, in a simplified form of the apparatus the apparatus could be designed to operate at fixed values for the parameters given, for example with stimulation staring at a time corresponding to any point within the range −15% to −5% of the R-R path length before the end of the T-wave, such as −10%, and with the train duration being selected at any time within the range of 5% to 15% o the R-R path length, such as 10% with it being insured that for the actual values chosen electrical stimulation stops at the latest at 5% of the R-R path length after the end of the T-wave. Such a simplified apparatus is also possible because the values selected will work to some extent on all patients.

In a preferred form of the apparatus of the invention, the pulses of each train of electrical stimulation have a pulse repetition frequency in the range of from 150 Hz to 350 Hz, preferably in the range from 170 Hz to 250 Hz and most preferably at 200 Hz.

In this connection the early publications by the present applicants suggest a frequency of 100 Hz. In practice the frequency that has been used is around 200 Hz. In actual fact there is a significant prejudice in the art against using frequencies above 100 Hz. This can be seen from the publications:

"Functional electrical stimulation of lower limbs in patients with chronic heart failure" by A. Karavidas published in Heart Fail. Rev. (2010) 15:563-579 summarizes all recent EMS studies, demonstrating the preference for frequencies of between 10 Hz and 50 Hz.

Moreover, "Electrical Stimulation Using Kilohertz-Frequency Alternating Current" by A. R. Ward published in Phys. THER. 2009; 89:181-190, claims that stimulation above 50 Hz leads to high frequency-related muscle fatigue such that the muscle stops working.

Effect of Burst-Mode Transcutaneous Electrical Nerve Stimulation on Peripheral Vascular Resistance by Barbara J Morgan, Julie E Sherry, Kristin M Oehrlein, Kristin S Hegge in PHYS THER. 2001; 81:1183-1191.

That document is concerned with transcutaneous electrical nerve stimulation well known under the acronym "TENS". TENS is typically used for alleviation of pain and there have been reports that TENS can affect the peripheral vascular system. As specified in the above referenced publication there are reports to the effect that three forms of TENS applied at the motor threshold result in muscle contractions. These three forms are (high frequency 85 pulses per second [pps], low frequency 2 pps, and burst mode with 2 bursts per second [bps]) actually decreased blood flow in subjects with no known pathology.

It is noted in the publication that burst-mode TENS stimulates peripheral nerve fibers using relatively high carrier frequencies (80-100 pps), modulated burst frequencies (2-5 bps), and intensities above or below the motor threshold. This pattern of external stimulation is said to more closely mimic physiologic sympathetic nerve activity than continuous-mode high or low-frequency stimulation does. The purpose of the study described in the publication was to investigate the effects of burst mode TENS on calf blood flow, arterial pressure, and skin temperature in subjects with no known pathology.

A burst frequency of 2 bps, a carrier frequency of 85 pps, and a phase duration of 250 microseconds were used. During one trial TENS was just below the motor threshold (ST), in another trial TENS was just above the motor threshold (MT), and in another trial TENS was 25% above the motor threshold (125% MT). The motor threshold for each nerve was defined as the analog reading on the electrical stimulator at the lowest intensity that elicited a visible muscle contraction. For the ST trial, the intensity was first increased to the motor threshold, then decreased until the muscle contraction disappeared. For the 125% MT trial, the TENS analog output used for motor threshold stimulation was multiplied by 1.25.

The cited publications leads one to the conclusion that 100 Hz as a carrier frequency is too high to be effective and that high stimulation intensity above the motor threshold is necessary.

Electrical muscle stimulation (EMS), also known as electro-myostimulation, neuromuscular electrical stimulation (NMES) and functional electrical stimulation (FES), is a form of muscle stimulation eliciting muscle contraction using electric impulses. EMS has received increasing attention in the last few years, because it has the potential to serve as a strength training tool for healthy subjects and athletes and a preventative and rehabilitation tool for partially or totally immobilized patients and patients with cardiovascular disease (Maffiuletti et al; European Journal of Applied Physiology 2011).

The impulses are generated by a device and delivered through electrodes on the skin in direct proximity to the muscles to be stimulated. The impulses mimic the action potential coming from the central nervous system, causing the muscles to contract. The electrodes are generally pads that adhere to the skin. It was discovered that the body functions induced by electrical stimulation caused long-term changes in the muscles. To this effect Soviet sport scientists applied EMS in the training of elite athletes in the '60s, claiming 40% force gains (Ward 2002).

However EMS, as it is used today, has several limitations:
1. EMS is non synchronized stimulation and operates both during systole and diastole thus increasing heart rate and blood pressure (i.e. an increase in rate-pressure-product) thereby increasing the heart load and therefore oxygen demand, for this reason EMS's use is limited to relatively early stage heart failure.
2. Whilst EMS treats the peripheral (skeletal muscle) component of CHF, it has little or no effect on the central (cardiac function and hemodynamic) components.

It should also be noted that EMS (FES) is typically operated by applying a continuous train of rectangular pulses of 50 Hz frequency at 120V amplitude and with 40 to 80 mA of current to a patient. This has been described by workers in the field such as Sherry in 2001, Filippatos in 2008, and by Karavidas in 2010.

Again one can see that the EMS pulse repetition frequency is relatively low. Workers in the field have also told the present applicants that frequencies above 100 Hz make no sense. Accordingly, it is considered highly surprising that frequencies above 150 Hz are not just highly effective but also allow effective stimulation at the motor threshold with beneficial results and no discomfort to the patient. Also, it has been found that despite using stimulation voltages as low as 5 to 8V the currents flowing are of the order of 40 mA. This is a surprisingly low voltage, since specialists not only consider the frequency above 150 Hz to be too high, but the voltage used is well below the accepted minimum level of 120 V. In fact the voltage and current values used by the present applicants at the higher frequencies they are operating at correspond to an effective skin resistance of approx. 200 ohms. Experts in the field propound the theory, based on the voltage and current values they use at lower frequencies, that the skin resistance is 2500-3000 ohms!

Particularly surprising is the present applicants finding that their seems to be a type of microwave effect at frequencies in the preferred range which not only lowers the effective skin resistance but also avoids fatigue and allows the muscles to be effectively stimulated at the motor threshold without having to go to 25% above MT as proposed by Sherry.

Preferably a voltage applied at the plurality of electrodes is less than ±15V, more specifically the voltage applied is in a range of from 6 to 10V and a current applied at the plurality of electrodes is less than 50 mA typically 30 to 40 mA. In this respect the current is maintained constant and the voltage applied is varied patient specific until muscle contractions are perceived. The stimulation pulses are advantageously provided with an average pulse duration of a pulse applied at the electrodes is in the range of 400 to 600 μs in particular of around 500 μs and at a frequency (pulse repetition frequency of 200 Hz. The effective skin resistance of the electrodes is found to be in a range of 180 to 300Ω, more specifically in a range from 200 to 250Ω.

Selecting the above parameters ensures that the microwave-like effect of the high frequency is achieved, leading to reduced 'effective' resistance of the skin, and allowing the electrical energy to penetrate deeper and wider, thereby reaching more muscle groups and increasing exercising and pumping efficiency.

The decision to choose a frequency of around 200 Hz as the optimal frequency was based on the following:

The discovery that the use of incrementally higher electrical frequencies above 150 Hz: led to an unexpected effect, namely a reduced skin and muscle resistance (ohms=volts/amps), which is now understood to be a penetrating, microwave-like effect with the locally effected part of the body acting like a waveguide. Also it has been found that operating at higher frequencies above 150 Hz has a beneficial effect on the reflected pulse pressure wave. This is shown by a reduction in aortic systolic pressure (which is actually increased due to cardiovascular disease) and an increase in aortic early diastolic pressure and coronary perfusion. Nevertheless, an upper frequency limit exists due to the fact that higher frequencies progressively increase the rate at which muscle fatigue (failure) is reached.

This is a further highly surprising discovery. The applicants have made many attempts to achieve muscle contraction for a longer period of time, and to prolong muscle contraction with a decreased energy input. They have now surprisingly discovered that with stimulation with a pulse repetition frequency in the new frequency range the duration of stimulation per heart cycle can be significantly reduced with significant benefits, particularly when the timing of the onset of stimulation is improved. The reduction in the duration of the stimulating trains of pulses also means that less electrical energy is required which leads to prolonged battery life prior to the need for recharging, a significant factor for a portable apparatus. Moreover, and especially surprising, is the fact that stimulating pulses with the timing and duration as described also synchronize with the patient's MSNA (muscle sympathetic nerve activity) and that this yields particularly beneficial effects with regard to the down regulation of MSNA and RAAS.

In a preferred apparatus of the present invention the duration of each train of electrically stimulating pulses is selected to correspond to a time in the range from 5 to 15%, preferably from 8 to 12% and especially at 10% of the R-R path length duration.

In a preferred embodiment the electrodes are adapted to be positioned in the vicinity of the motor points related to the larger muscles of a patient's leg.

The decision to relocate the site of stimulation of electrodes was based on the following recognitions:
a) the realization that the underlying mechanism was electrical muscle stimulation and not the previously claimed, unproven concept of electrical blood vessel wall stimulation;
b) the recognition that moving the electrodes to the midpoint (centre) of the larger calf and thigh muscles both reduced the current (voltage) needed and increased efficacy, whilst increasing comfort (reducing discomfort) of the patient.

The motor points at which muscles can be stimulated are preferably motor points of the muscles selected from the group of muscles comprising: the rectus femoris muscle, the vastus medialis muscle, the vastus lateralis muscle, the gracilis muscle, the Sartorius muscle, the tensor fascia latae muscle, the iliopsoas muscle, the adductorus longus muscle the pectineus muscle, the gastrocnemius caput mediale, the gastrocnemius caput laterale muscle, the soleus muscle, the plantaris muscle, the peroneus longus muscle, the tibialis anterior, the gastrocnemius muscle the peroneus brevis muscle, the flexor hallucis longus muscle and the extensor digitorum longus muscle.

The above group indicates that the preferred muscle groups stimulated by means of the apparatus are associated with a human's leg. These muscle groups are selected in order to target the largest muscles thereby maximizing the number of muscle fibres reached with a single electrode. Each of these muscles has several motor points 'feeding' it. It is preferred if the electrodes are placed as close as possible to the motor points of these muscles, the motor points being close to the surface of the patient's body, so that the electrodes can have a maximum influence on the muscle group and hence on the patient.

In a further preferred embodiment at least first, second, third and fourth electrodes are provided, with said first and second electrodes being capable of being mounted at or approximate to respective motors points on a first leg of the patient and said third and fourth electrodes being capable of being mounted at or approximate to respective motors points on a second leg of the patient, the apparatus being adapted to apply trains of electrical stimulation pulses to the electrodes in accordance with one of the following schemes:

all electrodes in parallel;

all electrodes in series;

all electrodes of the first leg followed by all electrodes of the second leg;

one electrode on the first leg followed by one electrode on the second leg, followed by another electrode on the first leg and another electrode on the second leg;

one electrode on the first leg followed by another electrode on the first leg, followed by one electrode on the second leg followed by another electrode on the second leg;

one electrode on the first leg in parallel with one electrode on the second leg, followed by another electrode on the first leg in parallel with another electrode on the second leg;

all electrodes randomly.

Such patterns prevent the human body from becoming accustomed to the stimulation pattern and, if the not all the muscles are stimulated for each heartbeat, the different stimulation patterns also prevent fatigue of the muscle.

In this connection the stimulation electrodes are preferably attached at the motor points of the following muscles: the vastus medialis muscle, the vastus lateralis muscle, the flexor hallucis longus muscle and the extensor digitorum longus muscle.

Alternatively the electrodes are applied at the motor points of the rectus femoris and of the gastrocnemius caput mediale.

These two different muscle groups are selected as they are the largest muscles in a humans leg and to date have shown the most promising stimulation results. In addition to the foregoing the applicants have found that much the best position for the electrodes is rather different from the positions on the torso previously used. Indeed the preferred positions on the legs are important having regard to the exploitation in accordance with the invention of the pulse pressure wave concept to be described later Both preferred methods of stimulation thus apply electrodes on both the thigh muscles and also the lower leg muscles of a patient. It is believed that alternately pulsing the lower leg and then the upper leg or vice versa relative to the end of the T-wave improves the efficacy of the heart's pumping and coronary perfusion mechanisms, thereby enabling the heart to pump an increased volume of blood at a lower systolic pressure and heart rate. This causes a reduction in heart work load and thus improves the patient's general health.

The apparatus is preferably adapted to operate the respectively selected scheme within one heartbeat, within subsequent heartbeats or within a plurality of heartbeats.

The apparatus is advantageously adapted to provide a predefined time delay between sequential trains of stimulation pulses applied to the plurality of electrodes.

In a further preferred embodiment the patient's muscle sympathetic nerve activity (MSNA) is detected and the amplitude peaks are used as a trigger for the initiation of the electrical stimulation relative to the end of the T-wave.

It has been recognized by the present applicants that the muscle sympathetic nerve activity is in synchronization with the T-wave of a patient's heartbeat and hence this can be detected by minimally invasive micro-neurography in order to recognize the position of the T-wave of a patient and thus provide stimulation at the desired time and for the desired duration relative to the T-wave. In this case micro needles monitor the muscle sympathetic nerve activity in thigh or calf muscles of a patient. Thus this method of detection provides an alternative to the cardiac cycle synchronized detection of the T-wave. Equally the peaks of the MSNA can be used as a surrogate marker to ensure the ideal values for the start and duration of electrical stimulation are chosen for the particular patient undergoing treatment.

Yet a further method of detecting the position of the T-wave includes tonometry. In this case the shape of the pulse pressure wave of a patient can be used to initiate and optimise the stimulation. For example, changes in aortic peak systolic pressure (systolic pressure augmentation), early diastolic pressure (shown by the magnitude of the diastolic notch and representing the coronary perfusion pressure) and aortic end diastolic pressure (measure of systemic vascular resistance) can be monitored and used for this purpose.

The total number of stimulating pulses of each train of pulses typically lies in the range from 10 to 50.

In the apparatus of the invention the trains of stimulating pulses are preferably applied to the patient for each cycle of the heart. They can, however, instead be applied for each second or third cycle of the heart, or for a periodically or randomly repeating cycle of the heart.

The apparatus is adapted in known manner to generate the electrical stimulation pulses in the form of biphasic pulses.

As indicated above it is a particular advantage of the apparatus of the present invention that treatment can be effected using electrical stimulation pulses with a peak amplitude selected or selectable to lie at the motor threshold at, i.e. at a value corresponding to muscle contraction just perceivable by the patient or by an observer.

In a further preferred embodiment either a separate ground electrode is provided or one of the plurality of electrodes is selected to operate as a ground electrode or selected ones of the plurality of electrodes are sequentially operated as ground electrodes.

Providing electrodes which occasionally operate as a ground electrode has the effect that the muscle associated with the ground electrode is not permanently subjected to the stimulation and hence is prevented from becoming accustomed to the stimulation. Moreover, not stimulating the same muscle for each heart cycle means that the duration of stimulation can be increased since fatigue of the muscle is also prevented.

Thus, as is known from an earlier application of the present applicants, a plurality of active electrodes can also be provided and they can be activated in a predetermined sequence or randomly to avoid the body becoming accustomed to the stimulation and not responding appropriately. It seems, however, that with the low stimulating voltage that can be used in the special frequency range of the present apparatus, there is little tendency for the response of the patient to drop off during prolonged treatment so that just one active electrode and one earth or ground electrode (passive electrode can be used). As noted above the improved apparatus in accordance with the present invention involves a shorter duration of the stimulation per heart cycle and this itself contributes to preventing the patient's response from dropping off due to accustomization (tolerance). The use of just two electrodes per leg is of course particularly beneficial as the cost for the electrodes and the complexity of the cabling are significantly reduced.

The plurality of electrodes are preferably activated in a predetermined sequence or randomly.

The timing in accordance with the present invention as defined in claim 1 has proved to give the best results with a wide variety of patients and is critical in the sense that the T-wave or a corresponding reference datum needs to be clearly identified and used as a trigger for the start of the train of pulses. This can best be done by using an appropriate sensor to monitor the electrocardiogram for the patient and to determine from it the position of the T-wave to generate a trigger signal for initiation of each train of stimulating pulses. Alternatively, as stated above, a sensor capable of measuring the MSNA of the patient can be used, since it has been found that the peaks of the MSNA signal are very accurately correlated with the end of the T-wave. The same applies to the pulse pressure wave which can be monitored by tonometry. Hitherto the T-wave has been estimated from the position of successive R-R peaks of the electrocardiogram and by using the Bazett relationship. This is still feasible but it has to be appreciated that the Bazett relationship is not really a constant for all patients but needs to be determined specifically for the patient or class of patient in question.

With the advance in sensor design it is now considered feasible to detect the onset of the T-wave, i.e. the rising flank thereof, or at least the peak value, directly.

Although the apparatus of the present invention works well using externally applied electrodes, it can be beneficial to combine the apparatus of the invention with a cardio-stimulator such as a cardiomyostimulator, a pacemaker or a defibrillator when the patient is in any event fitted with one of these devices. Not only does such a combined device make sense because the electrocardiogram sensing apparatus is already present but also interference between two different devices can be suppressed and treatment can be discontinued when needed, for example during defibrillator activity.

In a preferred embodiment the stimulation is provided at the plurality of electrodes in a burst mode of stimulation. A burst mode of stimulation is generally regarded as physiological as it mimics the muscle sympathetic nerve activity.

In a very preferred embodiment the apparatus further comprises the combination with a device for providing a surrogate marker, which can be a device integrated with the apparatus or separate from it. The device can be selected from the group comprising a tonometer, a blood pressure monitor, a blood oxygen monitor, a weighing scale and micro needles monitoring a patient's MSNA.

Advantageously the surrogate marker is selected from the group comprising a pulse pressure wave, a blood pressure, a blood oxygen content, a body weight and a muscle sympathetic nerve activity.

The device for providing a surrogate marker is advantageously used in combination with the apparatus for the purpose of diagnostics and/or patient monitoring.

In order to communicate the device and the apparatus communicate via an interface, the interface being adapted for wired and/or wireless transmission. A Bluetooth or Wireless LAN interface are suitable communication protocols for wireless transmission, whereas cables could also be simply used to connect the device to the apparatus.

Surrogate markers are additional measurements that can be conducted in addition to the determination of the heart rhythm in order to provide additional diagnostic information.

Such surrogate markers enable the fine tuning of the treatment to optimize the treatment effect for the respective patient. For example the tonometer externally monitors the pulse pressure wave values, e.g. at the wrist, which non-invasively provides the aortic pressure curve, systolic and diastolic pressures, systolic pressure augmentation and the position of the diastolic notch are provided by the aortic pressure curve, i.e. by the tonometer.

It was recognized during the operation of the apparatus that the use of tonometry as a surrogate marker provider, created a means of: optimizing stimulation settings and general use of the device. Moreover, the efficacy of the treatment was optimized. Furthermore, it provides a further method of measuring the treatment results and hence the benefits of treatment, including the improvement in prognosis.

Thus, when using a tonometer which effectively measures the aortic blood pressure curve, the measurement signals can be evaluated to determine the position of a notch or of a theoretical notch position for a patient whose circulation has deteriorated in such a way that a notch is no longer visible. The position of the notch or the calculated position of the notch respectively, is directly related to the trailing flank of the T-wave and can thus be used to set the parameters of the apparatus so that stimulation takes place with the ideal timing of the electrical stimulation pulses as related at the end of the T-wave. Thus the apparatus can be adjust to ensure that stimulation is carried out efficiently and it is then found that the notch in the aortic blood pressure curve becomes visible again at the start of treatment. This is highly important. In the case of cardiovascular disease and related diseases such as renal dysfunction, the pulse pressure wave travels much faster than normal and arrives back at the heart during systole rather than during diastole. This increases the systolic pressure, cardiac workload and oxygen demand, whilst reducing early diastolic pressure (evident from the disappearance of the diastolic notch), coronary perfusion and left ventricular oxygen supply.

The apparatus of the present invention slows down the return of the pulse pressure wave to the heart, ensuring that it arrives during early diastole thereby reducing peak diastolic pressure, cardiac workload and oxygen demand and increasing aortic early diastolic pressure, coronary perfusion and left ventricular oxygen supply. Increasing skeletal muscle activity in the legs results in vasodilation of the major arteries causing the pressure wave to travel further with some of the energy of the wave being absorbed by the increased blood cushioning effect in the periphery with its subsequent ECG synchronized return to the heart during early diastole. This is confirmed by the reappearance of the diastolic notch in patients undergoing treatment.

As mentioned above another device used to provide a surrogate marker can comprise a blood oxygen monitor which tells us how much oxygen is present in the blood. The device monitors the blood oxygen levels during the stimulation. Stimulation may thus be varied to optimize blood oxygen levels.

In another particularly preferred embodiment the apparatus is adapted to increase diuresis reducing diuretic drug needs and the risk of kidney failure.

In a further aspect the invention also relates to an apparatus for diagnosing and/or monitoring a patient having a heart, a heart rhythm comprising periodically repeating Q, R, S and T waves of an electrocardiogram and a peripheral vascular system, said electrocardiogram exhibiting a repeating QRSTQ heart rhythm having a Q-T systole duration, a T-Q diastole duration and an R-R path length, said patient having a pulse rate corresponding to said R-R path length, the apparatus comprising a plurality of electrodes attachable externally or internally to the patient for electrically stimulating the patient non-invasively or invasively, in synchronization with the heart rhythm, by trains of electrical stimulation pulses applied to the patient, determining, for cycles of the heart rhythm, a time corresponding to the end of an associated T-wave, the apparatus being configured to apply trains of electrical stimulation pulses at a time within a range of −15% to −1% of the R-R path length before the end of the T-wave and having a train duration selected in the range of 5 to 15% of said R-R path length, so that the train of stimulation pulses ends at at most +5% RR after the end of the T-wave, the apparatus being in combination with a device or unit providing a surrogate marker.

Such an apparatus can be used at the home of the patient, at the place of work of the patient, or while the patient is travelling, without the need of hospitalization. This reduces healthcare costs and can improve the effectiveness of the therapy. This is because the patient can be monitored at home remotely or directly. If changes in the patient's condition arise that are detected by the apparatus, the patient and/or medical staff can be alerted to this change in condition, so that the treatment of the patient can be fine-tuned at home or indeed irrespective of where the patient is. This enables a patient to enjoy the comfort of his/her own home and go about his daily routine, even if the medical condition he/she is suffering of would previously have required hospitalization.

The apparatus for diagnosing and/or monitoring can be adapted in a similar manner as the apparatus designed for treating a patient.

In this connection it is preferred if the surrogate marker is selected from the group comprising a pulse pressure wave, a blood pressure, a blood oxygen content, a body weight and a muscle sympathetic nerve activity. Advantageously the apparatus and the device for providing a surrogate marker communicate via an interface, the interface being adapted for wired and/or wireless transmission.

The present invention also extends to methods of treating, diagnosing and/or monitoring a patient using the above referenced apparatus. Thus, a method for treating a patient is provided, the patient having a heart, a heart rhythm comprising periodically repeating Q, R, S and T waves of an electrocardiogram and a peripheral vascular system, said electrocardiogram exhibiting a repeating QRSTQ heart rhythm having a Q-T systole duration, a T-Q diastole duration and an R-R path length, said patient having a pulse rate corresponding to said R-R path length, there being at least first and second electrodes attach able externally or internally to the patient for electrically stimulating the patient non-invasively or invasively, in synchronization with the heart rhythm, by trains of pulses applied to the patient, the method comprising the steps of determining, for cycles of the heart rhythm, a time corresponding to the peak of the associated T-wave, applying trains of electrical stimulation pulses within a range of −15% to −1% of the R-R path length before the end of the T-wave and having a train duration selected in the range of 5 to 15% of said R-R path length, so that the train of stimulation pulses ends at at most +5% RR after the end of the T-wave. Such a method improves the arterio-ventricular coupling. This means it leads to a reduction in the cardiac workload and oxygen demand whilst increasing coronary perfusion and oxygen supply resulting in increased cardiovascular efficiency.

The method can be advantageously be used to treat patients having at least one of the following disorders, cardiovascular disease, heart insufficiency, kidney dysfunction hyperlipidemia coronary artery diseases peripheral vascular disease hypertension, renal dysfunction, diastolyic dysfunction, angina, diabetes, sleep apnea, central and reduced kidney function, vascular dementia, multiple sclerosis, or to treat patients who are bed ridden (e.g. due to muscle defects), or in wheelchairs, or hospitalized.

In this connection it should be noted that medical studies have shown that there is a relationship between vascular dementia and other kinds of dementia. In this way, it is believed that improving the blood flow through a patient's blood vessels, reduces the likelihood of vascular dementia and hence also of other kinds of dementia. Whilst dementias were previous considered to all be caused by nerve death in various areas of the brain, it has recently been discovered that a narrowing of blood vessels supplying blood and oxygen to the brain may cause 'vascular dementia' which is responsible for a very significant percentage of all dementias. Further, increasing blood supply to these oxygen-starved brain regions reverses the condition, at least partly.

Further advantageous embodiments of the invention and preferred apparatus for carrying out the method of the invention are set forth in the subordinate claims incorporated herein by reference.

Figure 1B:
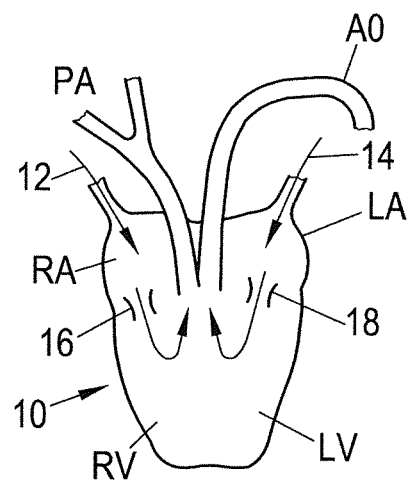
Figure 1C:
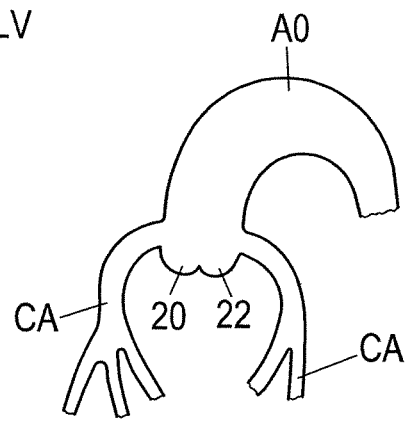
Figure 2:
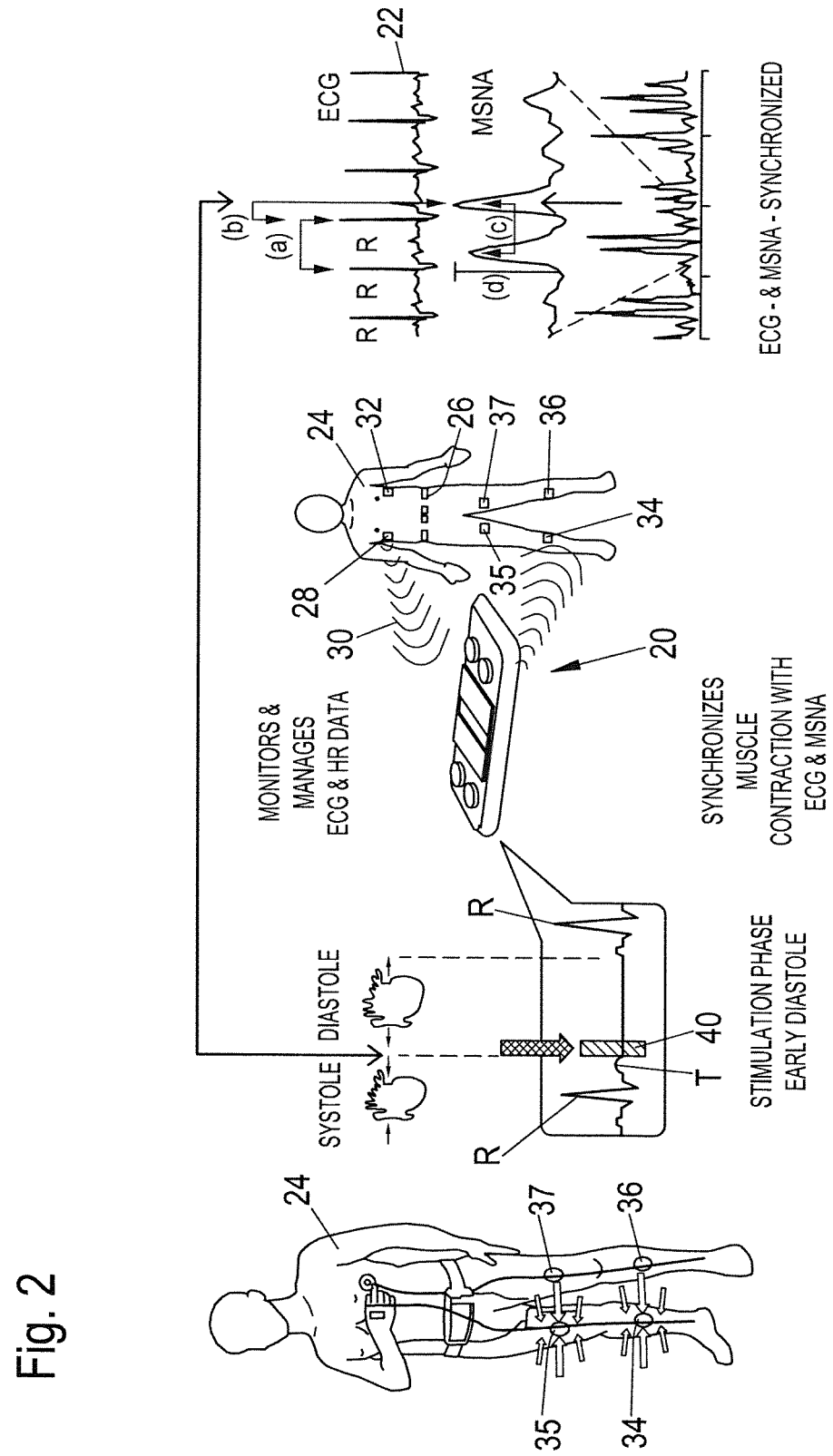
Figure 3:
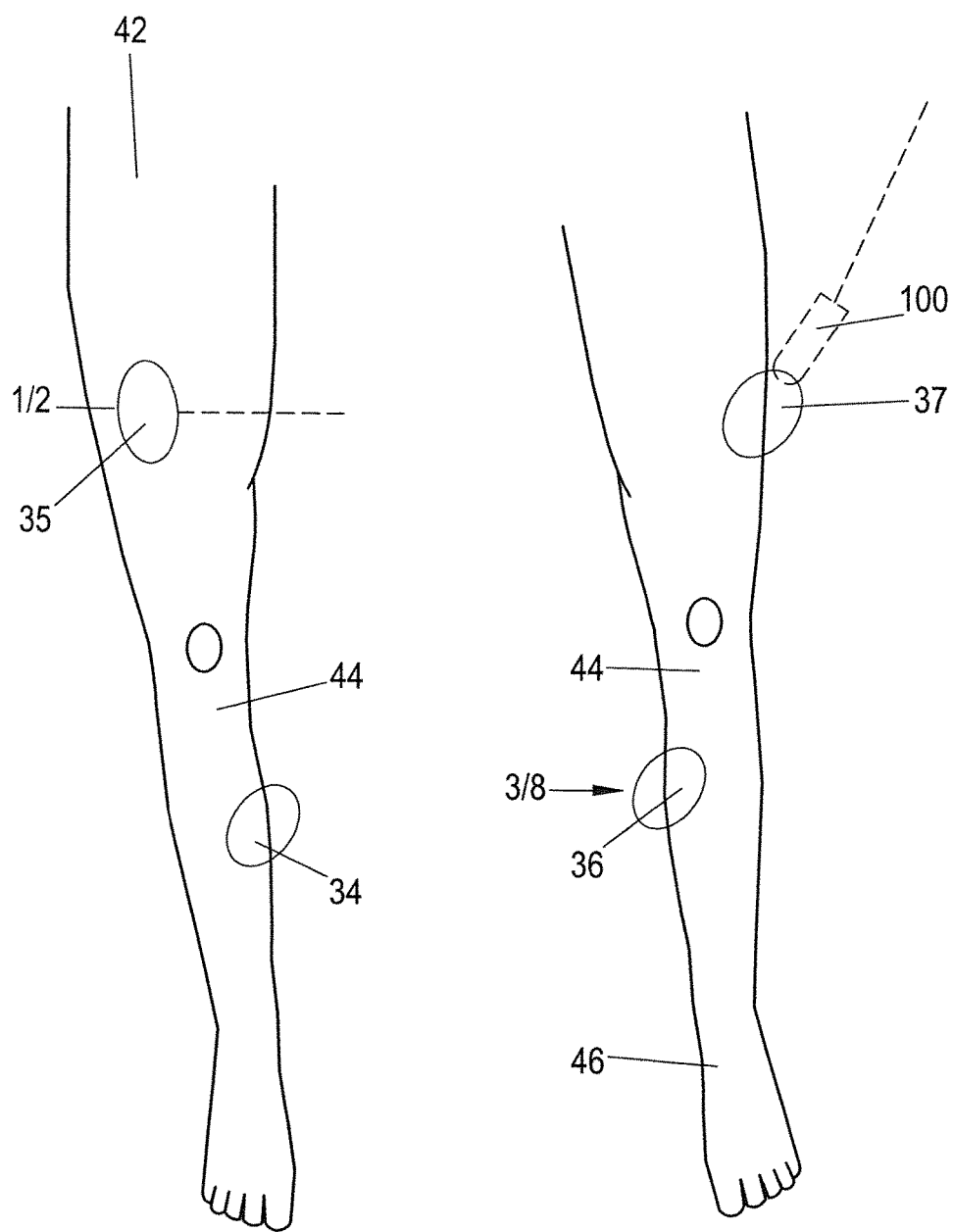
Figure 4:
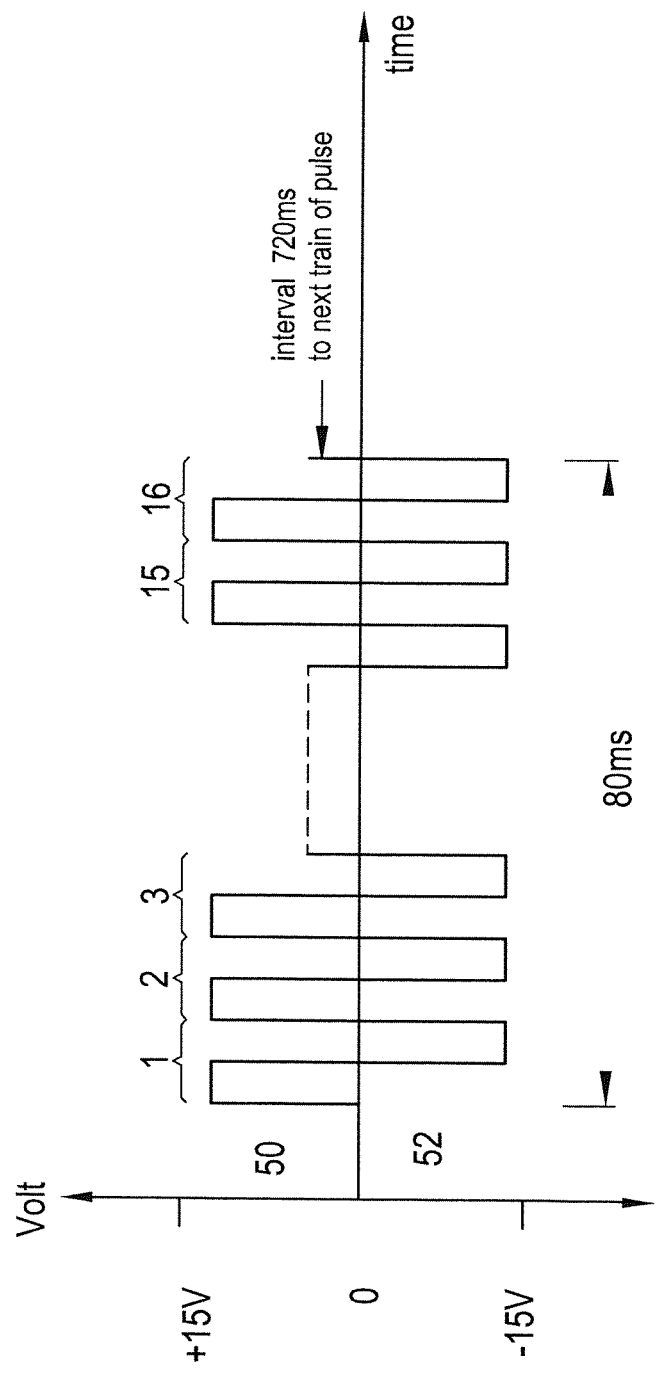

The invention will now be described in more detail having regard to the general layout of the apparatus, the mode of action of the apparatus, the evidence for the mode of action of the apparatus, the results of long term studies, lasting post treatment benefits and clinical results. More specifically the following description will be made by way of example only with reference to the accompanying drawings in which:

FIGS. 1A-1C are reproductions of FIGS. 1A-1C of U.S. Pat. No. 6,832,982 to assist in an understanding of the operation of the human heart, with FIG. 1 being a schematic diagram representative of an electrocardiogram, FIG. 1B being a schematic diagram of the human heart and FIG. 1C being an enlarged view of the aorta at the junction with the heart and the coronary arteries, FIG. 2 is a schematic diagram illustrating the use of an apparatus in accordance with the present invention, FIG. 3 a detailed view showing possible points of application of the electrodes on the human body FIG. 4 is a diagram explaining the design of the stimulating pulses applied generally at the end of the T-Wave in FIG. 2, FIG. 5 two different aortic pressure curves to show the presence and absence of the diastolic notch in patients of different ages, FIG. 6 a schematic representation of the human body illustrating the pulse pressure wave reflection zone, FIG. 7 a schematic diagram similar to FIG. 6 but showing a modified position of the pulse pressure wave reflection zone due to treatment with the apparatus of the invention, FIG. 8 a diagram relating the ECG of the patient of FIG. 7 when undergoing treatment and the synchronization with the patients MSNA, (MSNA synchronizes with the ECG), FIG. 9 an aortic pressure curve similar to FIG. 5 but now showing two sequential heart cycles for a patient before treatment and for the same patient during treatment, FIG. 10 pressure-volume loop plots for a patient before treatment (right hand loop) and for the same patients during treatment (left hand loop), FIG. 11 a series of diagrams similar to FIG. 10 but showing the dependence of the pressure-volume loop plots on the timing of the onset of electrical muscle stimulation by the trains of stimulating pulses, FIG. 12 a diagram illustrating the importance of the synchronization of the stimulation not just with the patient's ECG but also with respect to his MSNA, FIGS. 13a to 13d diagrams showing different types of schemes of trains of electrical stimulation pulses applied to first, second, third and fourth electrodes during one heart cycle, FIGS. 14a to 14g diagrams showing different types of schemes of trains of electrical stimulation pulses applied to first, second, third and fourth electrodes during a plurality of heart cycles, and FIG. 15 a comparison of the improvement in a patient's health using optimized drug therapy and optimized drug therapy in conjunction with the use of an apparatus in accordance with the invention.

To assist an understanding of the invention it is first necessary to consider the working of the human heart and the known prior art in this field.

The condition of the human heart is frequently measured by means of an electrocardiogram, the typical output trace that is obtained can, for example, be seen from FIG. 1A which reproduces FIG. 1A of U.S. Pat. No. 6,832,982. An electrocardiogram is basically a record of the sequence of electrical waves generated at each heartbeat and the different peaks of the typical electrocardiogram are usually designated by the letters P, Q, R, S and T. The so-called R-R path, i.e. the time between two R peaks represents one cycle of the heart and normally amounts to about 1 second.

Of particular interest is not only the R-R path, which corresponds to the frequency of the heart or the pulse rate, but rather also the Q-T path which reproduces the working performance of the heart, called the systole. The remainder of the path equivalent to R-R minus Q-T, i.e. T-Q effectively represents the recovery time of the heart in each heartbeat, called the diastole. The operation of the human heart is discussed later in more detail with reference to FIGS. 1A, 1B and 1C.

Cardiologists frequently refer to the concept of the heart workload (rate pressure product) which is the product of the heart rate, i.e. the frequency of R-R waves measured in heartbeats per minute, multiplied by the systolic blood pressure as measured in millimeters of mercury.

In the cardiosynchronized electrostimulation of muscles relative to the end of a T-wave—to which the present invention relates—the electric impulses are timed in such a way relative to the ECG that the heart and the stimulated muscles are contracting at different times, i.e. in the systole phase the heart is contracting and the stimulated muscles are relaxing, then, in the diastole phase the heart is relaxing and the stimulated muscles are contracting.

Important for the present invention is the determination of the time at which the T-wave occurs. There are several basic ways in which the end of the T-wave can be established from the point of view of triggering each new train of stimulating impulses. In the first case the T-wave can be directly detected, for example, from an electrocardiogram and the trains of pulses can be triggered relative to the position of the T-wave.

Alternatively, other reference points on the electrocardiogram can be recognized, for example the position of the Q-waves or the R-peaks, and a suitable delay to the end of each respective T-wave can then be calculated, since the length of the Q-T path has a known fixed relationship to the length of the R-R path referred to as the Bazett relationship. The trains of stimulating impulses are then triggered before the calculated ends of the T-waves. Details of pulse generation and triggering within a window determined in relation to the position of the end of the T-wave are given in the applicants earlier patents, for example in U.S. Pat. No. 6,832,982 and will not be repeated here. Instead only those aspects of the present invention which differ from the prior art arrangement will be discussed here.

Another way of establishing the timing of the stimulation is to detect the patient's MSNA and to analyze it to find the amplitude peaks which have been found to correlate with the T-waves, i.e. generally coincide with the middle of the descending section of the T-waves or are synchronized with them. These amplitude peaks can then be used as a trigger to initiate stimulation.

Yet another way of establishing the timing of the stimulation is to determine the shape of the patient's pulse pressure wave using tonometry. Thus stimulation can be started just before the projected position of the diastolic notch.

Since the start of stimulation coincides with the closure of the aortic valve, the closure of this valve could be detected with a phonocardiogram and used to initiate stimulation.

Win all the above mentioned cases it can be expedient or indeed necessary to look at a plurality of historical valued for a number of heartbeats and to predict the start of stimulation algorithmically from such data, for example by forming a sliding average value over several preceding heartbeats.

The duration of each train of stimulating impulses is preferably selected to amount to 5 to 15% of the R-R path length of a normal human being at rest. This leads to a duration of muscle stimulation of between 40 ms and 120 ms if the R-R path length is assumed to be 800 ms corresponding to a heart rate at rest of 75 beats per min.

Returning now to FIGS. 1A, 1B and 1C, a brief description of the normal operation of the human heart will now be given in order to facilitate an understanding of the present invention.

The heart 10 shown in FIG. 1B has four chambers, namely the right atrium RA, the right ventricle RV, the left ventricle LV, and the left atrium LA. Venous blood returning to the heart flows into the right atrium, then into the right ventricle and passes to the lungs via the pulmonary artery PA. In the lungs the blood picks up oxygen and returns to the left atrium LA, as indicated by the arrow 14. From there, the oxygenated blood passes into the left ventricle, and then into the aorta AO where it starts on its journey through the so-called big circulation around the body. The circulation from the right ventricle to the lungs and then to the left atrium is called the minor circulation.

The operation of the heart is associated with electrical signals, which are shown on the electrocardiogram of FIG. 1A. The point P signifies the contraction of the two atriums RA and LA, which pushes blood into the respective ventricles RV and LV via the respective valves 16 and 18, which act as non-return valves. The section of the electrocardiogram starting with Q and ending with T is referred to as the systole and represents the ventricle contraction which serves to expel blood from the right ventricle into the pulmonary artery, and from the left ventricle into the aorta. During this contraction, the valves 16 and 18 are closed to prevent reverse flow into the right atrium and left atrium. The section TQ is referred to as the diastole, meaning the relaxation or expansion of the ventricles. The heart is supplied with oxygenated blood via the coronary arteries CA, which branch off from the aorta just upstream of the aortic valves 20, 22, which close to prevent blood returning from the aorta to the left ventricle during the diastolic phase. Clearly the heart, itself a muscle, must be supplied with oxygenated blood to keep the muscles working. The heart is supplied with this oxygenated blood via the coronary arteries CA during diastole. The valves 20, 22 of the aorta AO close during the descending section of the T-wave and at this time the blood pressure in the aorta causes blood to enter the coronary arteries CA. Accordingly, an increase of the pressure in the aorta AO during diastole favors the coronary arteries.

In young healthy individuals the aortic pressure is increased during early diastole by the return to the ascending aorta of the reflected pulse pressure wave increasing coronary perfusion and oxygen supply. In a patient with cardiovascular disease the reflected pulse pressure wave arrives back in the ascending aorta much earlier, during systole, increasing aortic systolic pressure and left ventricular workload and oxygen demand, thereby reducing aortic early diastolic pressure, coronary perfusion and oxygen supply leading to a steady worsening of cardiovascular disease.

Turning now to FIG. 2 an outline of a possible manner of operation of an apparatus in accordance with the invention will now be given. At the center of FIG. 2 there is a schematic representation of the present applicant's m.pulse control unit 20 which is however modified in accordance with the present teaching. At the top right of the drawing there can be seen an electrocardiogram 22 measured from the patient 24 illustrated to the left of the control unit 20. In actual fact the electrocardiogram is measured by electrodes applied to the upper torso of the patient as indicated. The electrodes in this example are connected to a stimulation device 26 attached to a belt which passes on the measured electrocardiogram to the control unit 20 by means of wireless transmission. This is summarized by the central drawing which indicates that the electrodes 28, 32 mounted on the patient's chest transmit the electrocardiogram wirelessly to the control unit via the stimulation device 26 attached to the belt, this is symbolized by the family of curved lines 30. This transmission could however also take place by wire, optical cable or by direct wireless transmission (not shown). The control unit 20 then analyses the ingoing signals to predict the end of the next T-wave and transmits signals representing the end of the T-wave from the control unit 20 to the stimulation device 26 with associated electrodes 34, 35, 36, 37 present on the patient's legs. The stimulation device 26 then generates a train of pulses 40 as shown also in FIG. 4 and applies them to the electrodes as is also schematically shown by the pulses 40 indicated in the diagram to the left of and below the control unit 20 in FIG. 2. At the bottom right of FIG. 2 there is also a diagram labeled MSNA which shows the simultaneous synchronization of the train of pulses 40 with the patient's muscle sympathetic nervous system activity.

It should also be noted that the control unit could be implemented in an App on a smart watch, a smart phone, a tablet or another form of personalized electronic device (all not shown). In this way a patient would be provided with monitoring electrodes to measure the QRSTQ heart rhythm that communicate with the smart watch, smart phone or tablet etc. via either wired or wireless transmission and stimulation electrodes possibly including a signal generator (if this is not provided by suitable signals output by the smart watch, smart phone or tablet etc.) in order to stimulate the patient with the desired stimulation. The electrodes for stimulation can likewise be hard wired to or communicate with the signal generator and/or the control unit (e.g. smart phone App) via wireless transmission (e.g. Bluetooth). In this case the stimulation electrodes could be wireless stimulation pads or pads held in place via an elasticized band.

The control unit 20 can also be differently configured. For example the signal generator can be incorporated into the control unit 20 and can transmit the electrical stimulation pulses directly by wires (not shown) to the electrodes 1 and 2 or wirelessly.

An important consideration for the stimulation is the positioning of the electrodes 34, 35, 36 and 37. Whereas, in the past, the applicants have chosen to arbitrarily place the electrodes on the patient's leg (see e.g. the central illustration in FIG. 2) it has now been found that there are optimal positions of the electrodes 34, 35, 36, 37 on the patient's legs for ideal results with regard to the therapy, as indicated in FIG. 3. FIG. 2 also shows a schematic picture of the patient's legs 24 at the left of the sheet, with various positions marked on his upper and lower right and left leg for the electrodes 34, 35 and 36, 37 respectively. It should be noted that the positions of the electrodes can also be reversed.

FIG. 3 shows in more detail how the electrodes 34, 35, 36, 37 are preferably positioned. As shown in FIG. 3 the electrode 35 on the front of the upper right thigh is preferably positioned generally halfway along the thigh measured from the hip joint 42 to the knee joint 44 and one third of the way in from the outside of the thigh when viewed from the front. The electrode 34 on the lower right leg is placed generally at a position on the calf ⅜ of the way down the lower leg as measured from the knee joint 42 to the heel 46 and approximately ¼ of the way in from the inside of the calf when viewed from the rear. The electrodes 36 and 37 are placed with mirror symmetry on the left leg.

The optimized positioning of the electrodes as described in connection with FIG. 3 has, surprisingly, been found to permit a significant reduction in the stimulating voltage without reducing the efficacy of the treatment. The positioning of the electrode is preferably selected so that it is as close as possible to at least one motor point of the associated muscle. The ideal positioning results in the resistance (or capacitance (impedance)) between the muscle and the electrode reducing, whereby the voltage applied to induce the stimulation can be reduced while preserving the desired stimulating effect. Reducing the voltage applied is beneficial to the patient's well-being.

One convenient technique for identifying the motor points, as developed by the present applicant, comprises the use of a stylus that is attached to one of the stimulation leads and is moved around the expected vicinity of the motor point. On reaching the motor point it gives rise to muscle contraction. If no muscle contraction is noted, then the potential applied to the stylus via the lead is increased and the process is repeated, possible several times, until the muscle contraction becomes visible. If the stylus is then moved away from the point at which contraction becomes visible and the contraction stops then it is clear that the point at which the contraction became visible is as close as possible to the motor point. A suitable stylus 100 is schematically shown in phantom lines in FIG. 3. It should be noted that typical potentials used are in the range of 3 to 10V, preferably in the range of 4 to 6V.

In the scheme illustrated in FIGS. 2 and 3, the electrode 35 is connected as a ground electrode when stimulation is applied to the electrode 34 and similarly 37 is connected as a ground electrode when stimulation is applied to the electrode 36. Alternatively it is possible to provide one or more separate ground electrodes.

The form of the train of electrical stimulation pulses 40 preferably applied to the patient in the diagram of FIG. 2 is shown in FIG. 4. There the train of n pulses actually comprises n=16 ECG-synchronized biphasic pulses of amplitude 15V for the positive half wave 50 followed by −15V for the negative half wave 52. The duration of each pulse 50 plus 52 is 500 μs and the train of pulses thus has a total duration of 16×500 μs=80 ms. Assuming a heart rate of 75 cycles per minute there is therefore a spacing of 720 ms between the 16$^{th}$ pulse of the train of pulses shown and the first pulse of the next train of pulses 40 associated with the next heart-beat, i.e. starting at the end of the next T-wave. The pulse repetition frequency of the train of stimulating pulses is therefore 80 ms/500 μs=200 Hz So far as the amplitude of the biphasic signal is concerned, it has been found that different patients have different threshold voltages at which they perceive the muscle of becoming activated and at which the treatment is then preferably carried out. Thus, one possibility is for the operator 46 to vary the amplitude of the biphasic pulses until the motor threshold is reached.

Generally speaking, an amplitude of +15V for the positive half wave and of −15V for the negative half wave is expected but can vary from patient to patient so that it is usually set in practice each time a new patient is treated. The voltages used never exceed 45V. Preferably the range of voltages used is from 5 to 15V in dependence on the patient.

Measurements made using the preferred frequency (~200 Hz) and current values (~40 mA) of the present invention show that the amplitude of the voltage present during the stimulation is typically around 8V (16 V for the peak to peak value, i.e. from −8V to +8V). The skin resistance (impedance) appears to lie in the range from 100 to 900 Ohms Thus in this embodiment there is no pulse interval between successive pulses of the train of stimulation pulses.

A particularly important reason for using biphasic pulses is to avoid the onset of electrolysis in the tissue affected by the applied impulses. Any effects of this kind which may be triggered during one half pulse are immediately reversed in the next half pulse. Although biphasic rectangular pulses of the kind described above have been found to be satisfactory and currently represent the preferred type of pulses, they are by no means the only possibility. Generally speaking, it is anticipated that the pulses delivered by the pulse generator will be biphasic in the sense that they have some positive going signal component and some negative going signal component. However, it is not out of the question that single phase rectangular pulses can also be used with advantage in some circumstances. It is certainly not essential that the negative half wave is of the same size and shape as the positive half wave. The positive half wave could be of different amplitude and width from the amplitude and width of the negative half wave. Moreover, it is not essential for the pulses to be rectangular pulses. They could be sinusoidal or they could have some other shape if desired.

Figure 5:
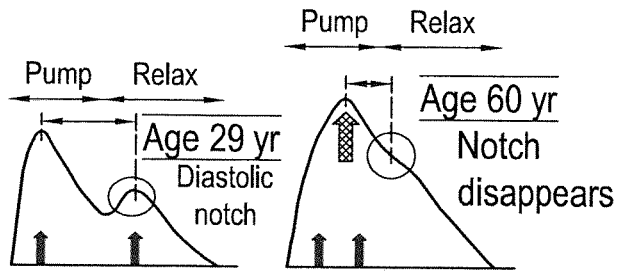

Turning now to FIG. 5 this diagram which reflects the work done by O'Rourke in 2007 and Karavidas in 2010, shows two different aortic pressure curves as a function of time over one heart cycle relating to the action of the pulse pressure wave. The left hand curve is typical for a twenty nine year old healthy patient and the right hand curve for an older patient of sixty years of age.

Various details can readily be seen from a comparison of these two curves. Firstly the peak blood pressure is higher in the older cardiovascular diseased patient than for the younger patient. The result of this is that the pumping phase is longer and the relaxation phase is shorter in the older cardiovascular diseased patient. In the young patient the reflected pulse pressure wave arrives during early diastole just after the aortic valve has closed increasing aortic early diastolic pressure (creating the diastolic notch), increasing coronary perfusion and increasing $LVO_2$ supply. This pronounced diastolic notch has almost disappeared in the older patient. Due to the early return of the reflected pulse pressure wave in the older patient, in fact during systole, the peak systolic pressure is increased (increasing workload and oxygen demand). This reduces the effect of the reflected pulse pressure wave during the early diastolic phase, leading to the disappearance of the diastolic notch, showing a reduction in early diastolic pressure, coronary perfusion and oxygen supply. These diagrams are helpful in understanding chronic heart failure (CHF) and in understanding that to be successful a therapy must address both the central and peripheral components of CHF.

The present applicant has reached a new understanding of how these aortic pressure diagrams of a patient suffering from a cardiovascular disease can be manipulated through the use of the apparatus of the present invention so that patients with cardiovascular problems can be given the ideal form of the aortic pressure curve for a younger person.

The present invention works by reversing this pathological process described above with reference to FIG. 5 by delaying the return of the pulse pressure wave. More specifically, the apparatus of the present invention activates the skeletal muscles. The activation of the skeletal muscles results in the of burning oxygen and glucose in the muscles and causes the release of vasodilatory substances which in turn causes a relaxation of the skeletal muscle blood vessels. This results in an increase in the blood supply to the stimulated area causing the pulse pressure wave to travel further delaying its return to the heart.

Figure 6:
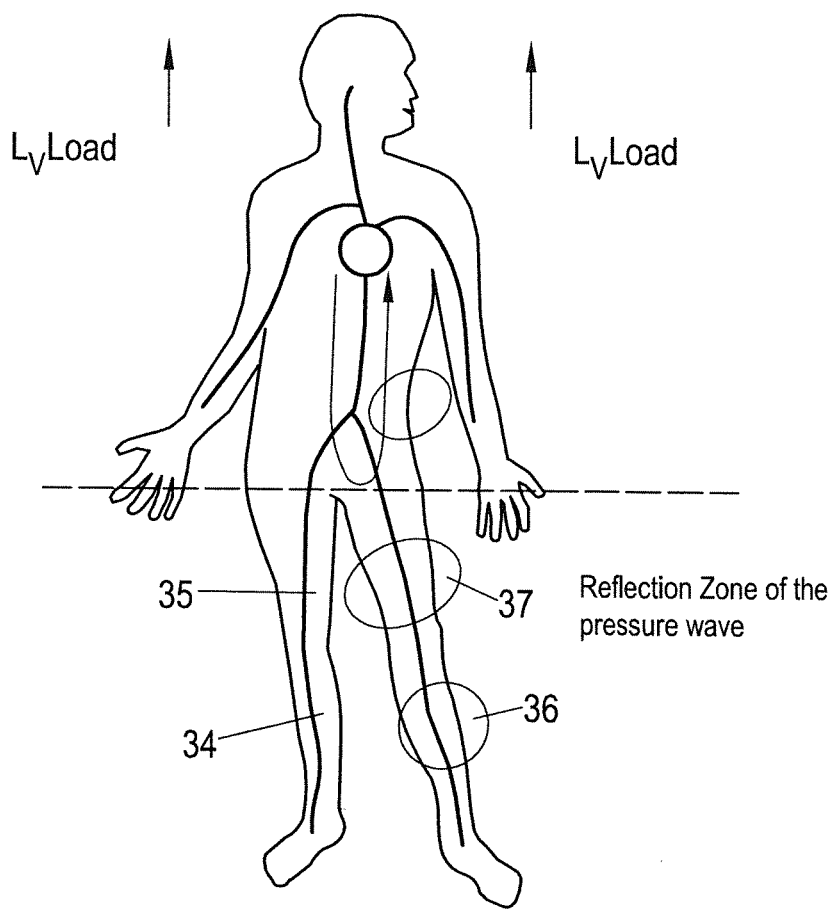
Figure 7:
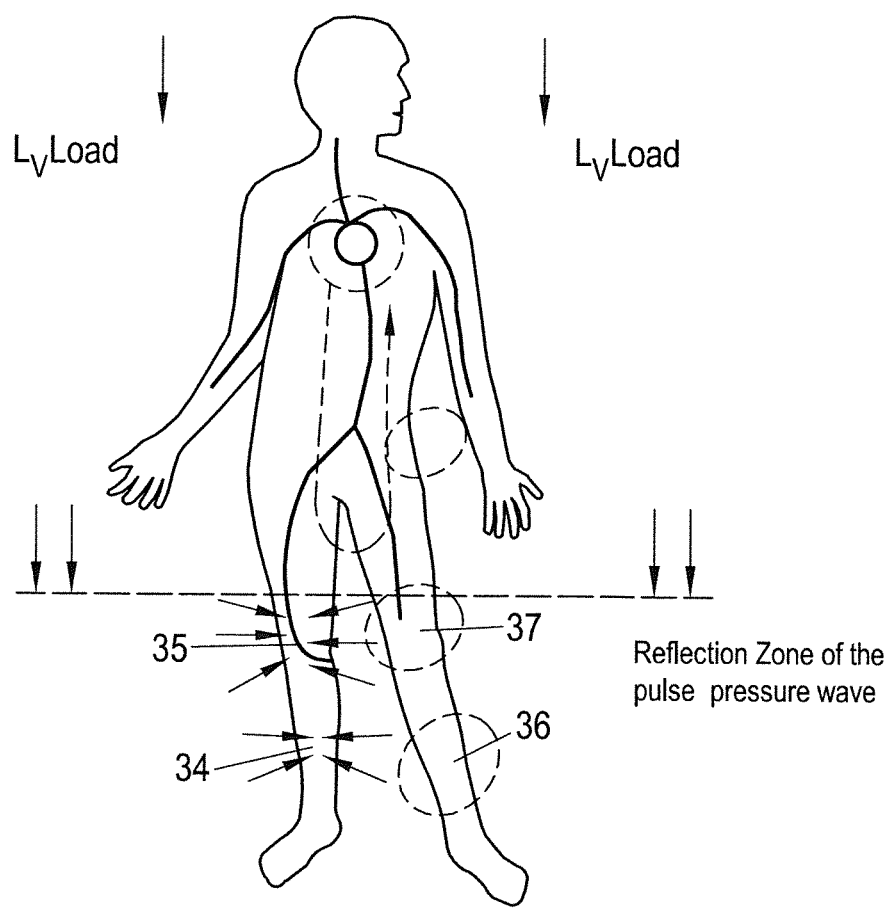

The additional blood in the stimulated area produces a cushioning effect reducing the energy of the pulse pressure wave (reducing pulse wave velocity) further delaying the return of the pulse pressure wave. Finally, the apparatus synchronizes the return of the pulse pressure wave to the heart during early diastole with the patient's ECG and MSNA due to the selected timing and duration of the train of stimulation pulses. The result of this is that the delayed return of the pulse pressure wave leads to a reduction in the aortic systolic pressure, LV workload and $LVO_2$ demand and to the reappearance of the early diastolic notch due to an increase in aortic diastolic pressure, an increase coronary perfusion and an increase in oxygen supply. This restores the arterio-ventricular coupling balance. FIG. 6 schematically illustrates a reflection zone of the elderly cardiovascular disease patient in FIG. 5 prior to treatment with the apparatus in accordance with the invention and how this is arranged at approximately the center of the torso. In contrast to this FIG. 7 schematically shows the situation following the treatment with the apparatus in accordance with the invention, where the reflection zone has been shifted lower in the body and thus causing the delay in the return of the pulse pressure wave. With more pathological disease (e.g. heart failure) there is an up-regulation of the sympathetic nervous system which increases systemic vascular resistance (vasoconstriction) causing the reflection zone to be shifted further up the patient's body causing an even earlier return of the pulse pressure wave.

With regard to the peripheral components of CHF it is noted that the decrease in cardiac output reduces the blood and oxygen supply to the kidneys and to the skeletal muscles. The kidney function is reduced, SNA (sympathetic nerve activity) and RAAS (renin-angiotensin-aldosterone system) are activated, increasing water and salt retention and SVR (systemic vascular resistance). Skeletal muscle function is disrupted as are physiological and metabolic dysfunction and ergoreflex hypersensitivity, resulting in increased SVR, exercise intolerance and breathlessness.

The down regulation of the sympathetic nervous system through the apparatus downregulates the renin-angiotensin-aldosterone system which results in increased diuresis (loss of water and salts) further unloading the heart. This is very beneficial if patients are suffering in an acute cardiovascular condition (e.g. acute decompensated heart failure). Treatment with such apparatus could be used, e.g. in a rescue vehicle, an emergency room and/or in an ICU. This can cause an almost instantaneous improvement in the patient's state by supporting their cardiovascular function, reducing cardiovascular damage and thus improving long term outcome.

So far as the peripheral components are concerned, SNA, ergoflex, and SVR are decreased and blood and $O_2$ supply to the kidneys and skeletal muscles are increased. The kidney function improves, RAAS is down-regulated, increasing water and salt excretion. Furthermore, the skeletal muscle function improves, and increases physiological and metabolic function, exercise tolerance and quality of life (QOL).

Figure 8:
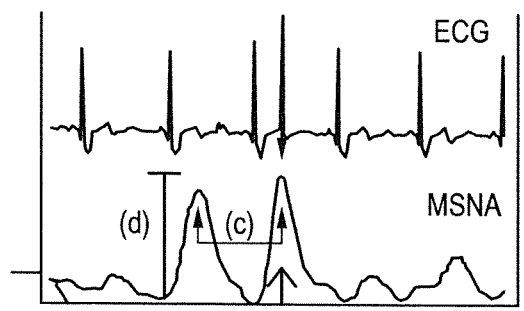

FIG. 8 shows how a patient's MSNA is synchronized with his ECG, more specifically with his T-wave. This fact can be used when determining the end of the T-wave or a corresponding reference point for the applied stimulation.

Figure 9:
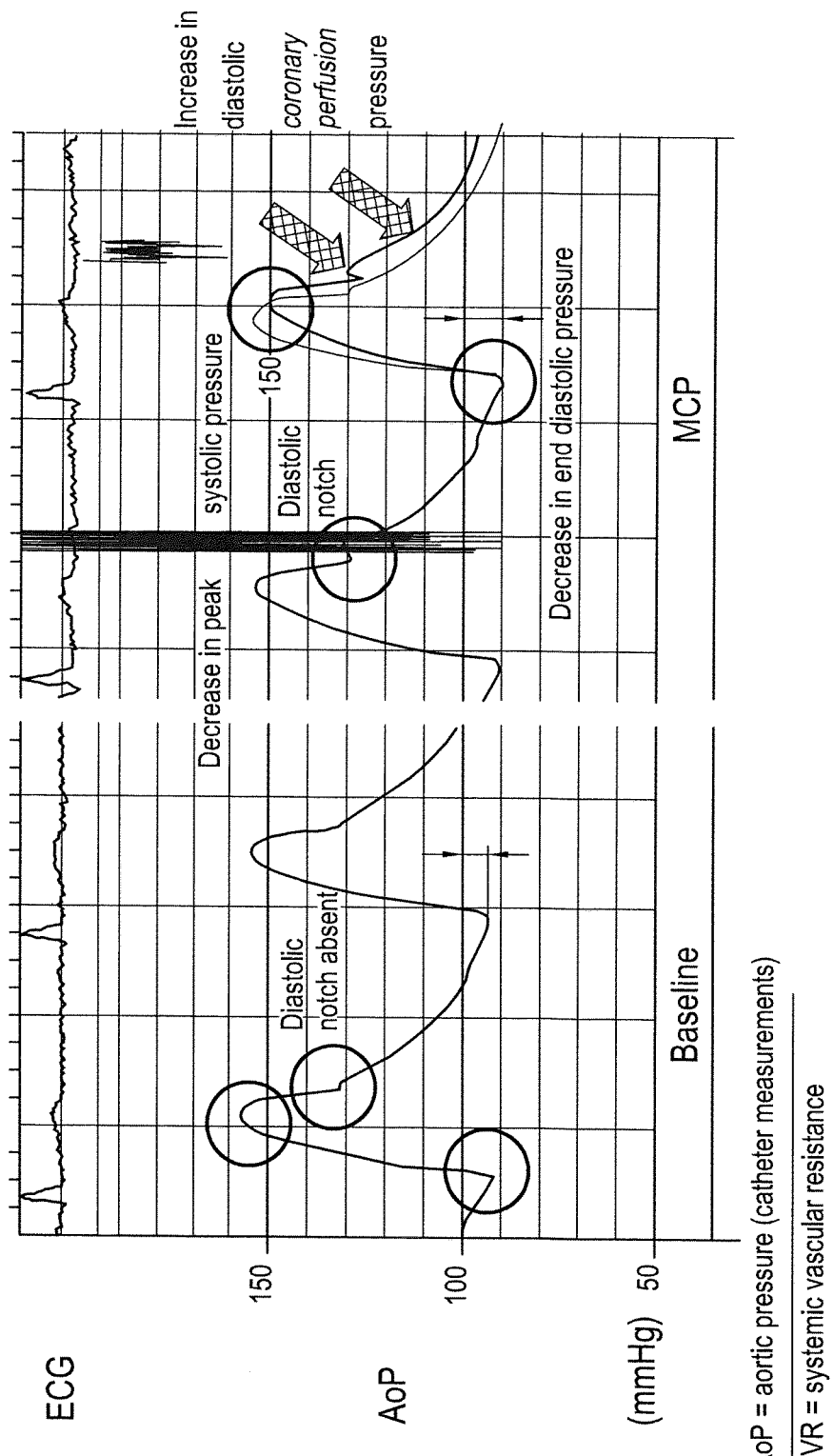

Reference is now made to FIG. 9 which shows diagrams similar to FIG. 5 but now showing pressure curves for two sequential heart cycles. The first diagram on the left labeled baseline corresponds to the right hand diagram of FIG. 5 for a sixty year old patient. Above this diagram there is shown the corresponding ECG which is drawn in in the correct phase relationship to the pressure curve. The second heart cycle is not drawn identically to the first because such curves normally vary from one heartbeat to the next. The blood pressure value indicated by the double arrows shows a lower blood pressure of 95 mm Hg. As was described in connection with the right hand diagram of FIG. 5 the diastolic notch is absent for the reasons given above.

The right hand diagram now shows the changes which result for the same patient during treatment with the apparatus in accordance with the present teaching (abbreviated here as MCP) and the phase relationship to the corresponding ECG. The two sequential heart cycles illustrated in the right hand diagram are not intended to suggest that the heart cycles follow one another immediately but rather illustrate the improvement after a short period of treatment.

These diagrams confirm the theory (mode of action of the apparatus) explained above. In particular they show the following:

a decrease in peak systolic pressure;

a decrease in end diastolic pressure;

an increase in diastolic pressure and thus coronary perfusion;

the return of the diastolic notch; and a decrease in the heart rate as a result of the heart working more efficiently.

The train of pulses 40, described above in connection with FIG. 4, are triggered before the end of the T-wave for each heart cycle. The peak blood pressure reduces fairly quickly (after a few minutes from the value of 158 mmHg shown in the left hand diagram to 150 mmHg due to a shift in the return of the pulse pressure wave to diastole. The diastolic notch reappears as a result of the ECG and MSNA synchronized delayed arrival of the pulse pressure wave. The lower blood pressure value (end diastolic blood pressure) reduces to just below 80 mmHg from 95 mmHg due to a reduction in SVR. The pressure peak is shifted to the right indicating a reduced heart rate. The shape of the falling flank of the curve is modified in relation to the corresponding flank shown in the left hand diagram, which has been drawn in in broken lines in the right hand diagram for the sake of easy comparison.

Thus the right hand diagram also shows significant decreases in both peak systolic pressure and in end diastolic pressure and an increase in diastolic coronary perfusion pressure.

Figure 10:
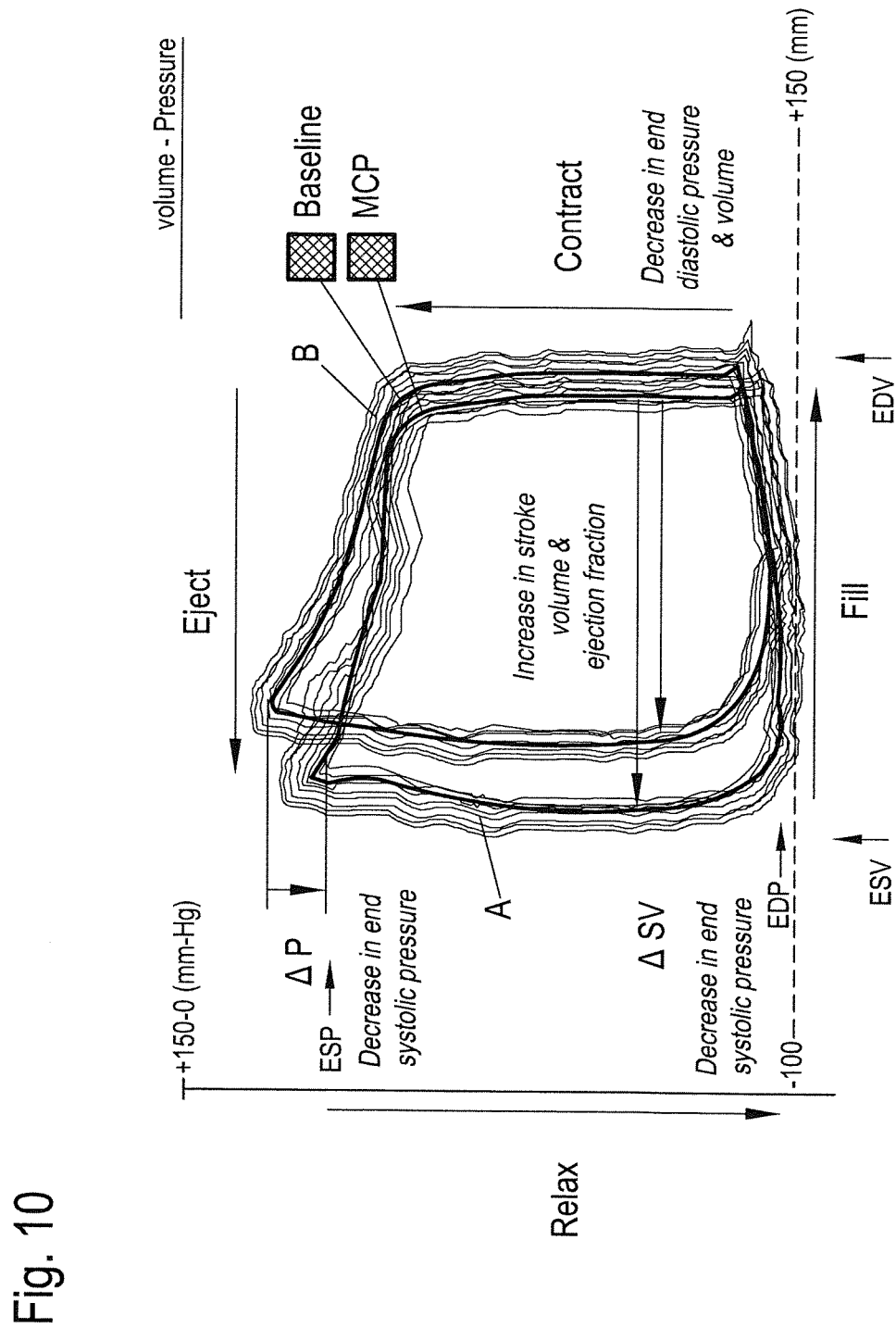

Turning now to FIG. 10 an explanation will now be given of a family of curves which explain other important parameters of the heart.

The diagram of FIG. 10 shows the operation of the heart of a patient treated using the therapy with an apparatus designed in accordance with the present applicant's earlier U.S. Pat. No. 6,832,982 in accordance with an investigation conducted by Walpoth and Hess in 2009. The curves shown in the diagram show pressure-volume plots for the left ventricle measured using a 6-F conductance catheter inserted into the left ventricle.

Two different-but related families of curves are shown, one family is for a patient before treatment with the apparatus of U.S. Pat. No. 6,832,982 and one for the same patient after treatment with the apparatus of U.S. Pat. No. 6,832,982. The two families of curves are closely similar at the right hand side of the diagram adjacent the vertical arrow labeled "contract". The contraction of the left ventricle is responsible for pumping the blood returning from the lungs into the right atrium out of the heart again into the aorta during the ejection stroke as indicated adjacent the arrow eject at the top of the diagram.

The vertical passage of the family of curves for the treated patients adjacent the arrow contract is however shifted slightly to the left relative to that of the untreated patients.

It can be seen from the diagram that for the untreated patients the ejection stroke is both of shorter duration and leads to a higher peak systolic pressure than for the treated patients. The pressure difference $\Delta P$ amounts to about 30 mmHg. There is therefore a significant decrease in the end systolic pressure ESP. At the left hand side of the diagram it can be seen that the family of curves for the treated patients is much further to the left than the family of curves for the untreated patients. This shows that the stroke volume, i.e. the quantity of blood ejected from the heart during the ejection phase and also the ejection fraction, i.e., the proportion of the blood in the heart which is ejected is considerably higher for the treated patients than for the untreated patients. There is thus a favorable differential in stroke volume $\Delta SV$ of about 12% for the treated patients. A result of this is that the treated patients have a larger decrease in the end systolic volume.

The ejection stroke is then followed by the filling stroke during which the left ventricle again fills with blood starting with the end systolic volume ESV and filling to reach the end diastolic volume EDV at the end of diastole corresponding to the bottom right hand point of the two families of curves. The minimum values for the two families of curves show the lowest blood pressure, the end diastolic pressure EDP. The small projection at the bottom right of the two families of curves is actually part of the family of curves for the treated patients and shows that these treated patients have a marked end diastolic pressure and volume.

Figure 11:
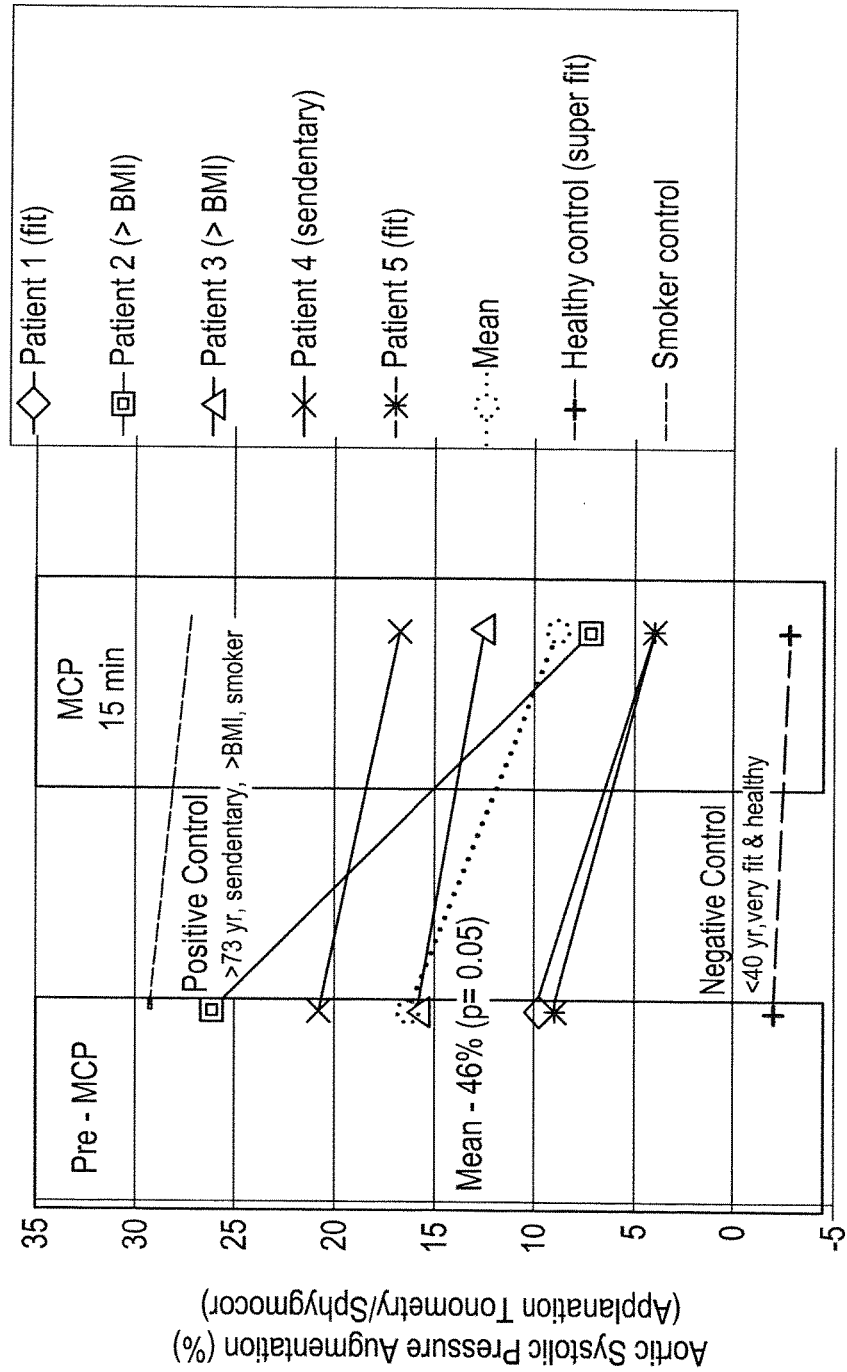

It is now interesting to review the diagrams of FIG. 11 which show diagrams similar to those of FIG. 10, but with the train of electrical stimulation pulses 40 having the preferred pulse repetition frequency, duration and amplitude in accordance with the invention but being applied at different times with only example 3 showing the time of application in accordance with the present invention. Each diagram has, immediately beneath it, a representation of the corresponding ECG showing the time at which the train 40 of stimulating pulses is applied. Again the diagrams show two families of curves one for a plurality of untreated patients and the second for the same patients with treatment.

Diagram 1 shows the situation when the trains of stimulating pulses are applied during each R-wave. It can be seen that the stimulation has no effect the two families of curves are fully superimposed.

Diagram 2 shows the situation when the stimulation 40 is applied during late systole, just before the T-wave. This application of the stimulation does result in an increase in the ejection fraction of the heart (left ventricle) which is positive and is in line with the findings on which the previous embodiments of the invention are based to the effect that timing of the start of duration in a period from late systole to mid diastole can be beneficial. Diagram 3 shows, as already indicated the timing of the present invention with particularly beneficial results. Diagram 4 also supports the earlier findings that stimulation starting in mid-diastole can also be beneficial. Diagram 5 shows that stimulation in late diastole has no effect and diagram 6 is simply a control with no stimulation which not surprisingly has no effect either. These diagrams thus confirm that cardiac cycle synchronisation between late systole and mid diastole is possible.

Figure 12:
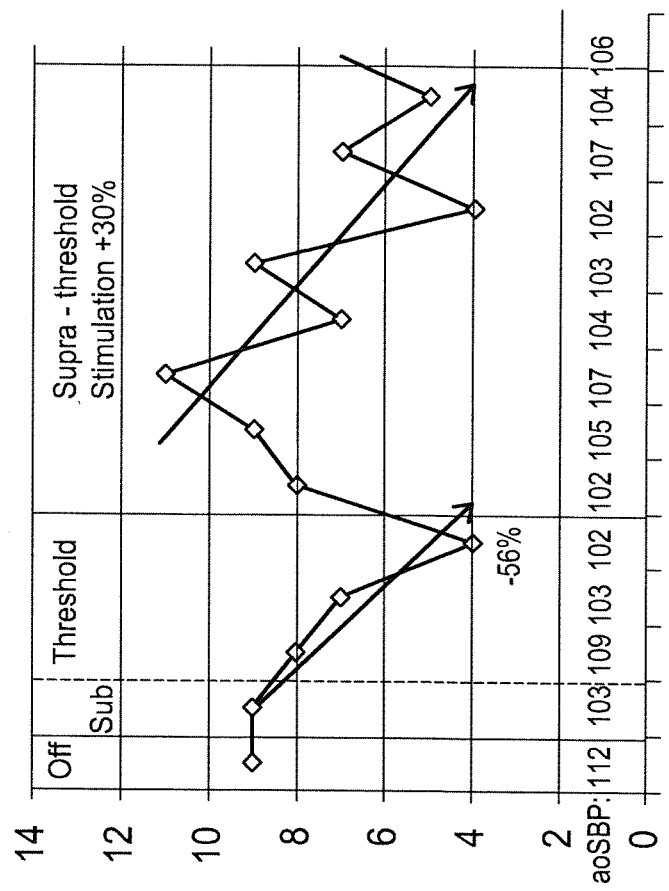

However, what was not appreciated and what is important for the present invention is the realisation that to achieve the maximum down regulation of MSNA, the range of stimulation which can be used is much narrower and falls into late systole. This is shown by the diagram of FIG. 12.

Figure 13A:
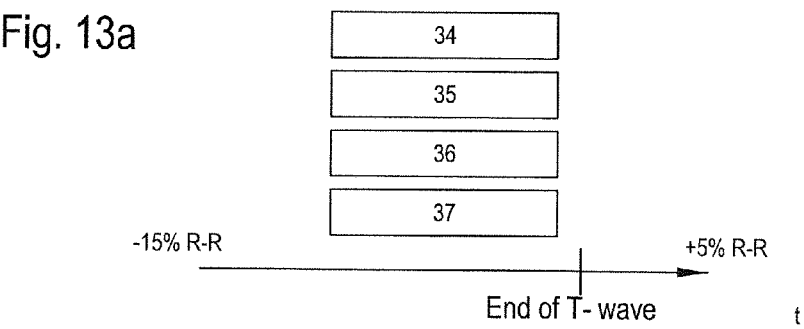
Figure 13B:
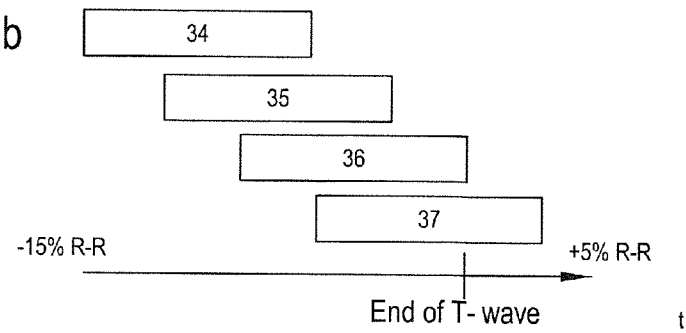
Figure 13C:
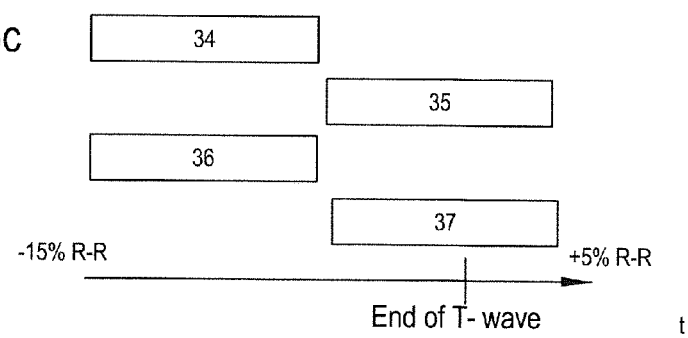
Figure 13D:
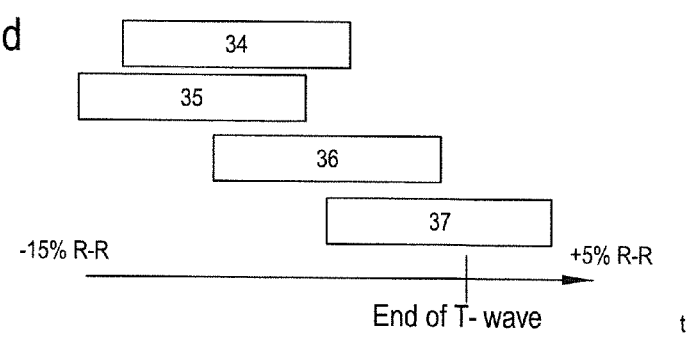

FIGS. 13*a* to 13*d* schematically show diagrams showing different types of schemes of trains of electrical stimulation pulses applied to first, second, third and fourth electrodes 34, 35, 36, 37. The trains of electrical stimulation pulses comprising a plurality of pulses are simply illustrated using a rectangular block. The first and second electrodes 34, 35 are mounted at or proximate to respective motors points on a first leg of the patient and the third and fourth electrodes 36, 37 are mounted at or proximate to respective motors points on a second leg of the patient. The schemes shown in FIGS. 13*a* to 13*d* are all provided during one heartbeat, more specifically within −15% R-R to +5% R-R from the end of the T-wave. FIG. 13*a* shows how the stimulation is effected at all electrodes 34, 35, 36, 37 in parallel; FIG. 13*b* shows how the stimulation is effected at all electrodes 34, 35, 36, 37 in series; FIG. 13*c* shows how the stimulation is effected at one electrode 34 on the first leg in parallel with one electrode 36 on the second leg, followed by another electrode 35 on the first leg in parallel with another electrode 37 on the second leg; and FIG. 13*d* shows how the stimulation is effected at one electrode 35 on the first leg followed by another electrode 34 on the first leg, followed by one electrode 36 on the second leg followed by another electrode 37 on the second leg. For the schemes of FIGS. 13*a* to *d* it is considered that a separate ground electrode is necessary, thus the electrodes 34, 35, 36, 37 are active electrodes.

FIGS. 14*a* to 14*g* schematically show diagrams showing different types of schemes of trains of electrical stimulation pulses applied to first, second, third and fourth electrodes 34, 35, 36, 37. The trains of electrical stimulation pulses comprising a plurality of pulses are simply illustrated using a rectangular block. The first and second electrodes 34, 35 are mounted at or approximate to respective motors points on a first leg of the patient and the third and fourth electrodes 36, 37 are mounted at or approximate to respective motors points on a second leg of the patient.

Figure 14A:
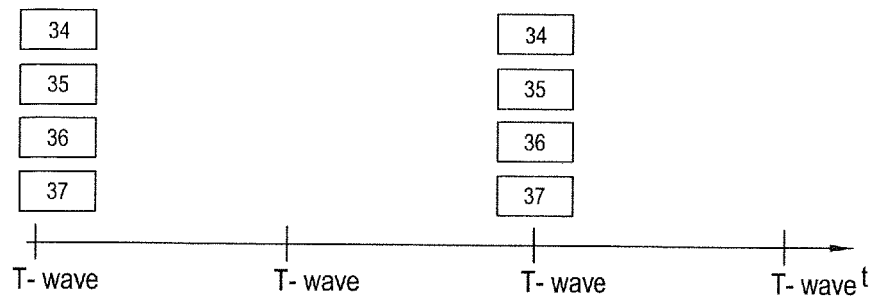
Figure 14B:
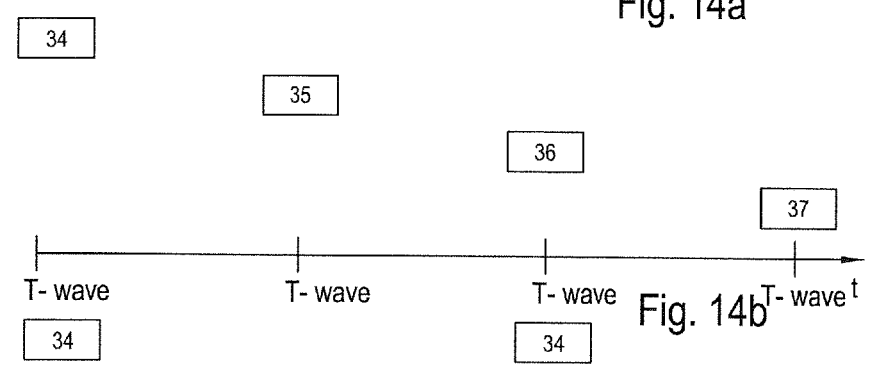
Figure 14C:
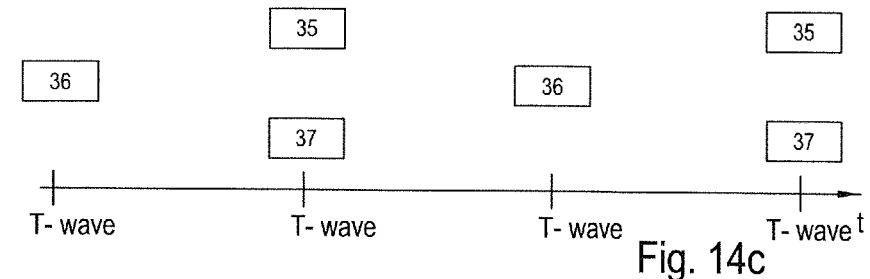
Figure 14D:
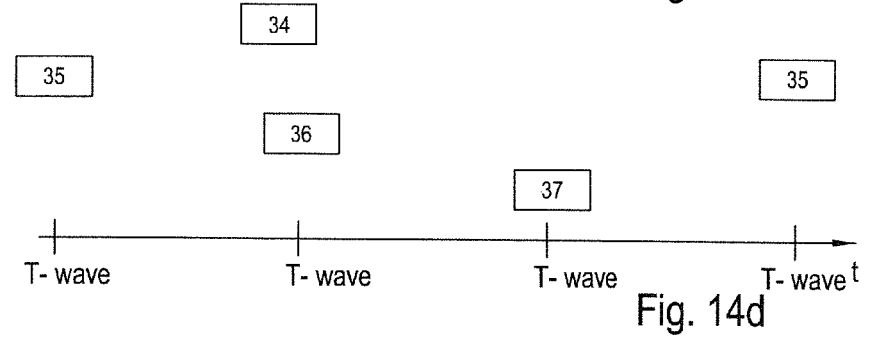
Figure 14E:
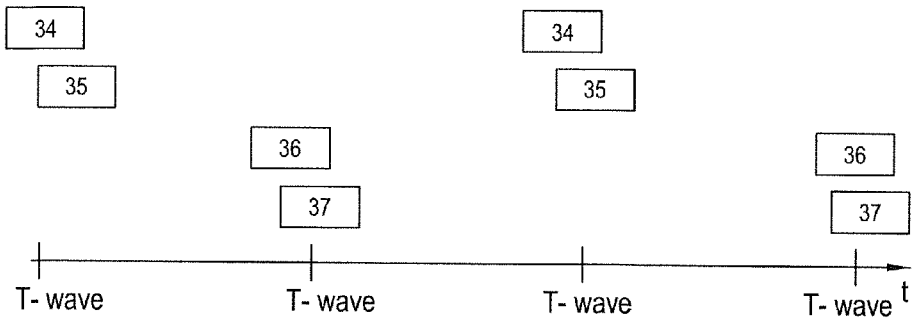
Figure 14F:
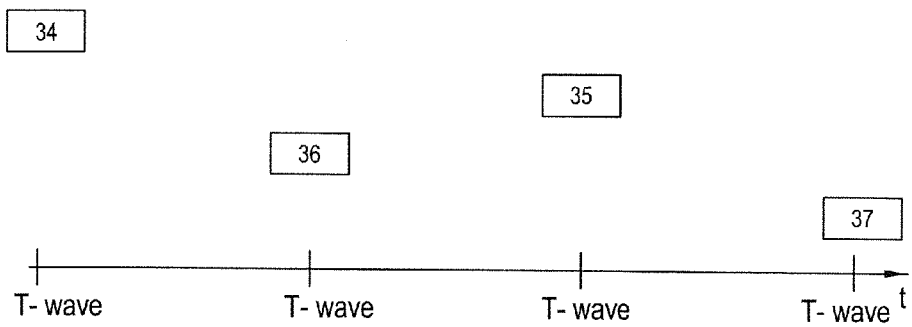
Figure 14G:
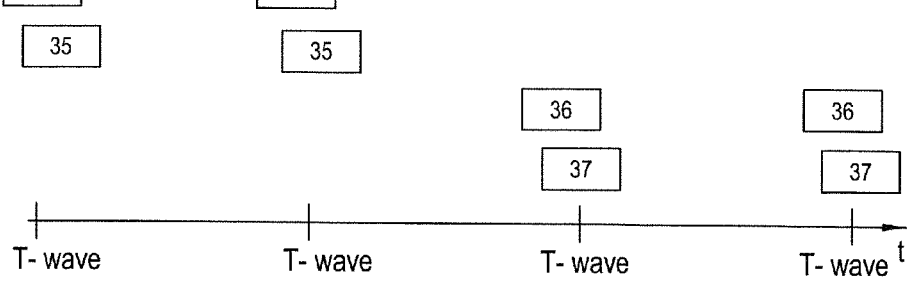

The schemes shown in FIGS. 14*a* to 14*g* are all provided over the course of four heartbeats, however, the stimulation is only provided during a time window of −15% R-R to +5% R-R from the end of the T-wave for each heartbeat and indeed starting at the latest at −1% R-R. FIG. 14*a* shows how the stimulation is effected at all electrodes 34, 35, 36, 37 in parallel; FIG. 14*b* shows how the stimulation is effected at all electrodes 34, 35, 36, 37 in series; FIG. 14*c* shows how the stimulation is effected at one electrode 34 on the first leg in parallel with one electrode 36 on the second leg, followed by another electrode 35 on the first leg in parallel with another electrode 37 on the second leg; FIG. 14*d* shows how the stimulation is effected at one electrode 35 on the first leg followed by another electrode 34 on the first leg, followed by one electrode 36 on the second leg followed by another electrode 37 on the second leg, this represents a random distribution of impulses. Such random cycles can be intermittently included in order to prevent the muscles from becoming accustomed to the stimulation. FIG. 14*e* shows how the stimulation is carried out on one leg during one heartbeat and on the other leg during the subsequent heartbeat etc., wherein the pulses administered at each leg are delayed with respect to one another in time; FIG. 14*f* shows a stimulation pattern in which one electrode 34 on the first leg is stimulated followed by one electrode 36 on the second leg, followed by another electrode 35 on the first leg and then followed by another electrode 37 on the second leg; and FIG. 14*g* shows a further scheme in which the two electrodes on each leg are sequentially pulsed.

Apart from the scheme of FIG. 14*a*, for which a separate ground electrode is required as for the embodiments of FIG. 13, in the other schemes of FIG. 14, i.e. FIGS. 14*b* to 14*d*, at least one of the electrodes to which a train of electrical stimulation pulses is not currently being applied can serve as a ground electrode. For example in FIG. 14*b*, while the electrode 34 is active, the remaining electrode 35 on that leg acts as a ground electrode and then when electrode 35 acts as an active electrode 34 is connected to act as the ground electrode. The same situation applies to the electrodes 36 and 37. It is also conceivable that all electrodes not currently in use are connected to act as a ground electrode in FIGS. 14*b* to 14*g*.

The stimulation patterns shown in FIGS. 13*a* to 14*d* can also be provided over the course of 6, 8, 10, 12 heartbeats etc. and pauses of stimulation can be included in the patterns and/or between each cycle of each scheme or one can provide stimulation only for every second, third, fourth etc. heart-beat. Alternatively different schemes can be combined to prevent muscle fatigue and the muscle from becoming accustomed to the stimulation (habituation). The electrodes 34, 35, 36, 37 can be applied at the legs of a patient in accordance with the positions e.g. schematically indicated in FIG. 3. This means the first electrode 34 can be applied on the left leg either in the region of the motor point of a muscle present at the calf, e.g. at the gastrocnemius caput medial or at the extensor digitorum longus muscle, the second electrode 35 can also be applied on the left leg in the region of a motor point of the thigh at e.g. at the vastus lateralis or at the rectus femoris muscle, the third electrode 36 is then applied on the right leg in the region of a motor point of the calf, i.e. at e.g. the gastrocnemius caput mediale of the right leg and the fourth electrode 37 is applied in the region of a motor point of the e.g. at either the vastus lateralis or the rectus femoris muscle of the right leg.

One particularly important recognition of the present invention is that the apparatus can be particularly beneficially used in a rescue vehicle, such as an ambulance, a helicopter or boat, and/or in an emergency room or intensive care unit. In this way a patient having suffered e.g. a heart attack or a suspected heart attack can be immediately treated at the start of the rescue operation and can be continued to be treated on his way into the emergency room and indeed in the emergency room pending attention by hospital staff. The early treatment of a heart disorder can be highly significant in stabilizing and improving the patient's condition, improving the flow of oxygenated blood to the heart muscle and in removing excess water from the patient's body, thus improving the chances of survival of a patient.

More specifically it has been found best if the at least one ground electrode 34 is applied externally to the patients lower left leg in the vicinity of the flex. digit. I. and flex. hall. I. muscles and if the at least one active electrode is applied externally to the patient's right thigh in the vicinity of the vast. lat. and vast. inter. muscles.

Figure 15:
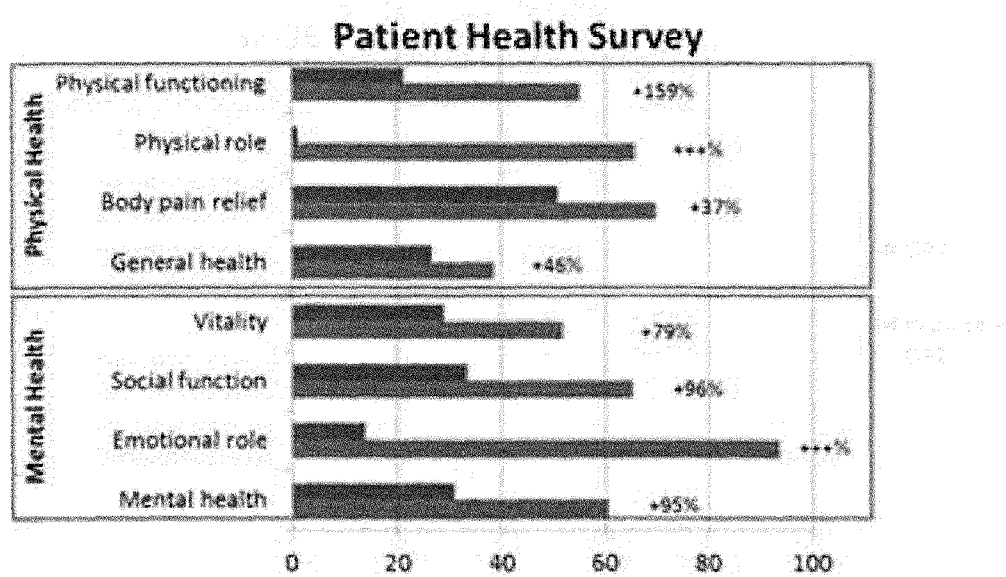

FIG. 15 shows a comparison of the improvement in a patient's health suffering from CHF when treated with optimized drug therapy (the respective top curve) and an optimized drug therapy in conjunction with the use of an apparatus in accordance with the invention (the respective bottom curve). As can clearly be seen the optimized drug therapy in conjunction with the use of the apparatus shows a significant improvement in a patient's mental and physical health on use of an apparatus in accordance with the invention during the treatment of CHF.

The present invention recognises that, to reduce healthcare costs and improve the effectiveness of therapy, there is a global move towards personalized medicine and patient empowerment (i.e. including the patient in the 'at home' management of his/her health). This has suddenly and dramatically increased the need for and the use of diagnostics in the home environment, to fine tune treatment and to identify when changes to treatment are needed in order to stop/reverse a deterioration in the patient's condition and the need for hospitalization.

The apparatus described here increases early diastolic pressure in the arteries feeding both the heart and the brain and clinical studies in both acute, decompensated heart failure and stable chronic heart failure have reported significant improvements in mental performance, leading to the belief that the present apparatus could provide significant benefits.

Special benefits of the present apparatus are the treatment capabilities of the apparatus for both cardiovascular and neurological conditions as well as diabetes, all of which are associated with the growing number of elderly, as well as the diagnostic and patient monitoring capabilities of the apparatus and the blue interface capabilities with diagnostic devices, including weight, BP and oximetry devices (associated or external).

The invention claimed is:

1. Apparatus for treating a patient having a heart, a heart rhythm comprising periodically repeating Q, R, S and T waves of an electrocardiogram and a peripheral vascular system, said electrocardiogram exhibiting a repeating QRSTQ heart rhythm having a Q-T systole duration, a T-Q diastole duration and an R-R path length, said patient having a pulse rate corresponding to said R-R path length, the apparatus comprising:

a control unit connected to a stimulation device further connected to a plurality of electrodes attachable externally or internally to the patient for electrically stimulating the patient non-invasively or invasively, in synchronization with the heart rhythm, by trains of electrical stimulation pulses applied to the patient, with the control unit of the apparatus being configured to determine, for cycles of the heart rhythm, a time corresponding to the end of an associated T-wave, and to transmit signals representing the end of the T-wave to the stimulation device, with the stimulation device being configured to generate and apply trains of electrical stimulation pulses at the plurality of electrodes at a time within a range of −15% to −1% of the R-R path length before the end of the T-wave and having a train duration selected in the range of 5 to 15% of said R-R path length, so that the train of stimulation pulses ends at at most +5% RR after the end of the T-wave, wherein a magnitude of a voltage applied at the plurality of electrodes is less than 15 V for the half wave of a biphasic pulse, and a current applied at the plurality of electrodes is less than 50 mA, and wherein the apparatus is configured to generate a pulse repetition frequency of each of the trains of electrical stimulation pulses in a range from 150 Hz to 350 Hz.

2. The apparatus in accordance with claim 1, wherein the duration of each of the trains of electrical stimulation pulses is selected to correspond to a time in the range from 8 to 12% of the R-R path length duration.

3. The apparatus in accordance with claim 1, wherein the stimulation device is configured to generate the electrical stimulation pulses in the form of biphasic pulses.

4. The apparatus in accordance with claim 1, the stimulation device is configured to generate the electrical stimulation pulses with a peak amplitude selected or selectable to lie at a value corresponding to a value perceivable by the patient as a muscle contraction.

5. The apparatus in accordance with claim 1, wherein either a separate ground electrode is provided, or one of the plurality of electrodes is selected to operate as a ground electrode or selected ones of the plurality of electrodes are sequentially or randomly operated as ground electrodes.

6. The apparatus in accordance with claim 1, wherein the stimulation device is configured to activate the plurality of electrodes in a predetermined sequence or randomly.

7. The apparatus in accordance with claim 1, wherein the electrodes are configured to be positioned in the vicinity of motor points related to the larger muscles of a patient's leg, or wherein the electrodes are configured to be positioned in the vicinity of motor points related to the larger muscles of a patient's leg wherein the larger muscles of a patient's leg are selected from the group of muscles consisting of the following members the rectus femoris muscle, the vastus medialis muscle, the vastus lateralis muscle, the gracilis muscle, the Sartorius muscle, the tensor fascia latae muscle, the iliopsoas muscle, the adductorus longus muscle the pectineus muscle, the gastrocnemius caput mediale, the gastrocnemius caput laterale muscle, the soleus muscle, the plantaris muscle, the peroneus longus muscle, the tibialis anterior, the gastrocnemius muscle the peroneus brevis muscle, the flexor hallucis longus muscle and the extensor digitorum longus muscle.

8. The apparatus in accordance with claim 1, wherein the stimulation device is configured to apply the trains of electrical stimulation pulses to the patient for each cycle of the heart, or for each second or third cycle of the heart, or for a periodically or randomly repeating cycle of the heart; or wherein the apparatus is configured to provide a predefined time delay between sequential trains of stimulation pulses applied to the plurality of electrodes or wherein the stimulation is provided at the plurality of electrodes in a burst mode of stimulation; or wherein each electrode is configured to apply the current of the trains of electrical stimulation pulses in a distributed manner to a muscle underlying the electrode.

9. The apparatus in accordance with claim 1, wherein at least first, second, third and fourth electrodes are provided, with said first and second electrodes being capable of being mounted at or approximate to respective motors points on a first leg of the patient and said third and fourth electrodes being capable of being mounted at or approximate to respective motors points on a second leg of the patient, the apparatus being adapted to apply trains of electrical stimulation pulses to the electrodes in accordance with one of the following schemes:

all electrodes in parallel;
all electrodes in series;
all electrodes of the first leg followed by all electrodes of the second leg;
one electrode on the first leg followed by one electrode on the second leg, followed by another electrode on the first leg and another electrode on the second leg;
one electrode on the first leg followed by another electrode on the first leg, followed by one electrode on the second leg followed by another electrode on the second leg;
one electrode on the first leg in parallel with one electrode on the second leg, followed by another electrode on the first leg in parallel with another electrode on the second leg;
all electrodes randomly.

10. The apparatus in accordance with claim 9, the apparatus being configured to operate the respectively selected scheme within one heartbeat, within subsequent heartbeats or within a plurality of heartbeats.

11. The apparatus in accordance with claim 1, wherein a current applied at the plurality of electrodes is less than or equal to 40 mA.

12. The apparatus in accordance with claim 1, wherein an average pulse duration of a pulse of one of the trains of electrical stimulation pulses is in the range of 400 to 600 μs.

13. The apparatus in accordance with claim 1, in combination with a device providing a surrogate marker, the surrogate marker being selected from the group comprising a heart rate, a pulse pressure wave, a blood pressure, a blood oxygen content, a body weight and a muscle sympathetic nerve activity; or wherein the apparatus is in combination with a device providing a surrogate marker (to fine tune the treatment), the surrogate marker being selected from the group comprising a heart rate, a pulse pressure wave, a blood pressure, a blood oxygen content, a body weight and a muscle sympathetic nerve activity, wherein the device is selected from the group comprising an ECG, a tonometer, a blood pressure monitor, a blood oxygen monitor, a weighing scale, micro needles monitoring a patient's MSNA and a tonometer adapted to measure an aortic blood pressure curve and to derive from it the position of a reflected pulse pressure wave relative to systole and stimulating the patient with the train of stimulation pulses such that the pulse pressure wave arrives back at the heart during systole; or wherein the apparatus is in combination with a device providing a surrogate marker, with the surrogate marker being selected from the group comprising a heart rate, a pulse pressure wave, a blood pressure, a blood oxygen content, a body weight and a muscle sympathetic nerve activity, wherein the device and the apparatus communicate via an interface, the interface being adapted for wired or wireless transmission.

14. The apparatus in accordance with claim 1, wherein the determination of the end of the T-wave is carried out in an evaluation unit using signals provided by a device selected from the group comprising an ECG, a tonometer, a blood pressure monitor, a blood oxygen monitor and micro needles monitoring a patient's MSNA; or wherein the patient's muscle sympathetic nerve activity (MSNA) is detected and the amplitude peaks are used as a trigger for the initiation of the electrical stimulation relative to the end of the T-wave.

15. The apparatus in accordance with claim 1, wherein at least one of the plurality of the electrodes is included in an article of clothing; and wherein the article of clothing is selected from the group of members comprising a pair of trousers, a belt, a tourniquet, a pair of shorts, a pair of socks, a pair of tights and a pair of dungarees.

16. The apparatus in accordance with claim 1, and adapted for use in a rescue vehicle or in an emergency room or intensive care unit.

17. A method of treating, diagnosing or monitoring a patient having a heart, a heart rhythm comprising periodically repeating Q, R, S and T waves of an electrocardiogram and a peripheral vascular system, said electrocardiogram exhibiting a repeating QRSTQ heart rhythm having a Q-T systole duration, a T-Q diastole duration and an R-R path length, said patient having a pulse rate corresponding to said R-R path length, using an apparatus comprising a plurality of electrodes attachable externally or internally to the patient for electrically stimulating the patient non-invasively or invasively, in synchronization with the heart rhythm, by trains of electrical stimulation pulses applied to the patient, determining, for cycles of the heart rhythm, a time corresponding to the end of an associated T-wave and applying trains of electrical stimulation pulses within a range of −15% to −1% of the R-R path length before the end of the T-wave and having a train duration selected in the range of 5 to 15% of said R-R path length, so that the train of stimulation pulses ends at at most +5% RR from the end of the T-wave,
    wherein a magnitude of a voltage applied at the plurality of electrodes is less than 15 V for the half wave of a biphasic pulse, and a current applied at the plurality of electrodes is less than 50 mA, and
    wherein the apparatus is configured to generate a pulse repetition frequency of each of the trains of electrical stimulation pulses in a range from 150 Hz to 350 Hz.

18. The method in accordance with claim 17, wherein the method is used to treat patients having at least one of the following disorders, cardiovascular disease, heart insufficiency, kidney dysfunction, renal dysfunction, diastolyic dysfunction, and reduced kidney function, or wherein it is used to treat odema by removing excess water and salts stored in the body.

* * * * *